United States Patent
Oda

(10) Patent No.: US 11,490,870 B2
(45) Date of Patent: Nov. 8, 2022

(54) RADIOGRAPHIC IMAGE DETECTION DEVICE, METHOD FOR OPERATING RADIOGRAPHIC IMAGE DETECTION DEVICE, AND PROGRAM FOR OPERATING RADIOGRAPHIC IMAGE DETECTION DEVICE

(71) Applicant: FUJIFILM CORPORATION, Tokyo (JP)

(72) Inventor: Yasufumi Oda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 157 days.

(21) Appl. No.: 17/179,427

(22) Filed: Feb. 19, 2021

(65) Prior Publication Data

US 2021/0275127 A1 Sep. 9, 2021

(30) Foreign Application Priority Data

Mar. 9, 2020 (JP) .............................. JP2020-040302

(51) Int. Cl.
*A61B 6/00* (2006.01)
*G06T 5/50* (2006.01)
(Continued)

(52) U.S. Cl.
CPC .......... *A61B 6/5258* (2013.01); *A61B 6/4233* (2013.01); *A61B 6/488* (2013.01);
(Continued)

(58) Field of Classification Search
CPC ..... A61B 6/5229; A61B 6/488; A61B 6/4233; A61B 6/5258; A61B 6/4283; A61B 6/585;
(Continued)

(56) References Cited

U.S. PATENT DOCUMENTS 10,136,873 B2 * 11/2018 Kawamura ............. G06T 5/002
10,172,583 B2 * 1/2019 Enomoto ............. A61B 6/4241
(Continued)

FOREIGN PATENT DOCUMENTS

JP 2014-168602 A 9/2014

*Primary Examiner* — Irakli Kiknadze
(74) *Attorney, Agent, or Firm* — Solaris Intellectual Property Group, PLLC

(57) ABSTRACT

A correction image acquisition process includes: a first gain image acquisition process of reading a pixel signal from a pixel region irradiated with radiation in a state in which a subject is not placed to acquire a first gain image; a pre-irradiation image acquisition process of reading the pixel signal from the pixel region in a state in which the subject is not placed and the radiation is not emitted to acquire a pre-irradiation image; a discarding process of discarding charge accumulated in a pixel of the pixel region after a dose of radiation that saturates the charge is emitted in a state in which the subject is not placed; a post-irradiation image acquisition process of reading the pixel signal from the pixel region to acquire a post-irradiation image after the discarding process is performed; and a second gain image acquisition process of subtracting the pre-irradiation image from the post-irradiation image to acquire a second gain image.

8 Claims, 19 Drawing Sheets

(51) Int. Cl.
  *G06T 5/00* (2006.01)
  *G01N 23/04* (2018.01)

(52) U.S. Cl.
  CPC ........... *A61B 6/5229* (2013.01); *G01N 23/04* (2013.01); *G06T 5/002* (2013.01); *G06T 5/50* (2013.01); *A61B 6/585* (2013.01); *G01N 2223/401* (2013.01); *G06T 2207/10116* (2013.01)

(58) Field of Classification Search
  CPC .. A61B 6/463; A61B 6/54; A61B 6/56; A61B 6/542; A61B 6/563; A61B 6/5241; A61B 6/4208; A61B 6/582; A61B 6/40; A61B 6/42; A61B 6/5205; A61B 6/548; G01N 23/04; G01N 2223/401; G01N 2223/303; G01N 2223/306; G01N 2223/304; G06T 5/002; G06T 5/50; G06T 2207/10116; G06T 7/0012; G06T 2207/30004; G01T 1/2018; H04N 5/32; H04N 5/341; H04N 5/361; H04N 5/3651
  USPC .......................................................... 378/62
  See application file for complete search history.

(56) References Cited

U.S. PATENT DOCUMENTS

| | | | |
|---|---|---|---|
| 11,153,511 B2* | 10/2021 | Tezuka | G01T 1/17 |
| 2009/0147921 A1* | 6/2009 | Okamura | A61B 6/5235 |
| | | | 378/98.12 |
| 2015/0192684 A1* | 7/2015 | Ito | G01T 1/20 |
| | | | 250/361 R |
| 2021/0011176 A1* | 1/2021 | Ishinari | G01T 1/247 |

* cited by examiner

RADIOGRAPHIC IMAGE DETECTION DEVICE, METHOD FOR OPERATING RADIOGRAPHIC IMAGE DETECTION DEVICE, AND PROGRAM FOR OPERATING RADIOGRAPHIC IMAGE DETECTION DEVICE

CROSS-REFERENCE TO RELATED APPLICATIONS

The present application claims priority under 35 U.S.C. § 119 to Japanese Patent Application No., 2020-040302 filed on Mar. 9, 2020. The above application is hereby expressly incorporated by reference, in its entirety, into the present application.

BACKGROUND

1. Technical Field

The technology of the present disclosure relates to a radiographic image detection device, a method for operating the radiographic image detection device, and a program for operating the radiographic image detection device.

2. Description of the Related Art

In the medical field, an X-ray imaging system that uses, for example, X-rays as radiation is known. The X-ray imaging system includes an X-ray generation apparatus that generates X-rays and an X-ray imaging apparatus that detects the X-rays, which have been generated by the X-ray generation apparatus and transmitted through a patient as a subject, to capture a radiographic image. The X-ray imaging apparatus includes an X-ray image detection device that detects an X-ray image based on the X-rays transmitted through the subject and a console that performs, for example, the control of the driving of the X-ray image detection device and the storage and display of the X-ray image.

The X-ray image detection devices include a direct conversion type that directly converts X-rays into charge and an indirect conversion type that converts X-rays into visible light and then converts the visible light into charge. In any of the types, the X-ray image detection device has a pixel region in which a plurality of pixels detecting X-rays are arranged and a reading unit that reads a pixel signal from the pixel region, and generates an X-ray image on the basis of the pixel signal read by the reading unit.

The X-ray image detected by the X-ray image detection device includes, for example, dark current noise generated in each pixel and fixed pattern noise generated by a charge amplifier and the like included in the reading unit. Offset data is acquired in advance before X-ray imaging in order to remove the noise components from the X-ray image. The offset data is acquired by reading the pixel signal from the pixel region in a state in which no X-rays are emitted. The offset data is data including only noise components. After the offset data is acquired, offset correction for subtracting the offset data from the X-ray image obtained by the X-ray imaging is performed to obtain an X-ray image from which noise has been removed.

Of the dark current noise and the fixed pattern noise included in the offset data, the dark current noise changes depending on the temperature. Therefore, a time interval from the acquisition of the offset data to the X-ray imaging is long. In a case in which the temperature changes during the time, a dark current noise component changes, which results in a reduction in the accuracy of offset correction. For this reason, it is ideal to acquire the offset data immediately before the X-ray imaging is performed, in order to improve the accuracy of offset correction.

However, in a case in which the offset data is acquired immediately before the X-ray imaging, a time lag occurs between the instruction to perform the X-ray imaging and the actual X-ray imaging. As a result, there is a possibility that the X-ray image intended by the radiographer will not be obtained. Therefore, a technique has been proposed in which an X-ray image detection device is driven in a time shorter than the irradiation time of X-ray imaging or in a binning mode to perform an offset data acquisition operation immediately before the X-ray imaging (see JP2014-168602A).

SUMMARY

JP2014-168602A discloses a configuration in which gain data (hereinafter, referred to as a gain image) is acquired in advance in order to correct, for example, a difference in the sensitivity of pixels to X-rays. In JP2014-168602A, gain correction is performed on a corrected X-ray image obtained by subtracting offset data (hereinafter, referred to as an immediately preceding offset image) acquired immediately before X-ray imaging from an X-ray image.

Instead of the gain correction method described in JP2014-168602A, it is considered that, after gain correction is individually performed on an X-ray image and an immediately preceding offset image, the gain-corrected immediately preceding offset image is subtracted from the gain-corrected X-ray image, in order to improve the accuracy of the gain correction. In this case, it is necessary to individually acquire gain data (hereinafter, referred to as a first gain image) for correcting the X-ray image and gain data (hereinafter, referred to as a second gain image) for correcting the immediately preceding offset image.

Since the immediately preceding offset image is an image acquired in a state in which no X-rays are emitted, it does not include a distribution of sensitivity caused by a difference in the sensitivity of the pixel to the X-rays and includes high frequency noise caused by a dark current flowing from the pixel to the reading unit. The second gain image needs to be an image indicating the high frequency noise caused by the dark current.

However, in general, the gain data includes both the distribution of the sensitivity of the pixel to the X-rays and the high frequency noise caused by the dark current. For this reason, the gain data acquired by the method according to the related art can be used as the first gain image, but is not capable of being used as the second gain image. Therefore, it is desirable to acquire the second gain image indicating the high frequency noise caused by the dark current with high accuracy, that is, to perform gain correction on the immediately preceding offset image with high accuracy.

An object of the technology of the present disclosure is to provide a radiographic image detection device that can perform gain correction on an immediately preceding offset image with high accuracy, a method for operating the radiographic image detection device, and a program for operating the radiographic image detection device.

In order to achieve the above object, according to an aspect of the present disclosure, there is provided a radiographic image detection device that includes a pixel region, in which a plurality of pixels that accumulate charge corresponding to radiation emitted from a radiation source to detect the radiation are arranged, and performs radiography, which irradiates the pixel region with the radiation from the radiation source in a state in which a subject is placed between the radiation source and the pixel region and reads a pixel signal corresponding to the charge from the pixel region, to acquire a radiographic image of the subject. The radiographic image detection device comprises at least one processor. The processor performs a correction image acquisition process of acquiring a correction image for correcting the radiographic image. The correction image acquisition process includes: a first gain image acquisition process of reading the pixel signal from the pixel region irradiated with the radiation in a state in which the subject is not placed to acquire a first gain image; a pre-irradiation image acquisition process of reading the pixel signal from the pixel region in a state in which the subject is not placed and the radiation is not emitted to acquire a pre-irradiation image; a discarding process of discarding the charge accumulated in the pixels of the pixel region after a dose of the radiation that saturates the charge is emitted in a state in which the subject is not placed; a post-irradiation image acquisition process of reading the pixel signal from the pixel region to acquire a post-irradiation image after the discarding process is performed; and a second gain image acquisition process of subtracting the pre-irradiation image from the post-irradiation image to acquire a second gain image.

Preferably, in the post-irradiation image acquisition process, after performing the discarding process, the processor repeatedly reads the pixel signal from the pixel region to acquire a plurality of the post-irradiation images. Preferably, in the second gain image acquisition process, the processor subtracts the pre-irradiation image from an average image obtained by averaging the plurality of post-irradiation images to acquire the second gain image.

Preferably, in the pre-irradiation image acquisition process and the post-irradiation image acquisition process, the processor reads the pixel signal from the pixel region in an accumulation time shorter than that of the plurality of first gain images or using binning reading to acquire the pre-irradiation image and the post-irradiation image.

Preferably, the correction image acquisition process further includes: a first offset image acquisition process of reading the pixel signal from the pixel region using the same reading method as that used for the first gain image in a state in which the subject is not placed and the radiation is not emitted to acquire a first offset image for correction; a second offset image acquisition process of reading the pixel signal from the pixel region using the same reading method as that used for the second gain image in a state in which the subject is not placed and the radiation is not emitted to acquire a second offset image for correction; and an immediately preceding offset image acquisition process of reading the pixel signal from the pixel region using the same reading method as that used for the second gain image immediately before the radiography to acquire an immediately preceding offset image for correction. Preferably, the processor performs: a primary correction process of subtracting the first offset image from the radiographic image to generate a primary corrected radiographic image; an offset difference image generation process of subtracting the second offset image from the immediately preceding offset image to generate an offset difference image; a secondary correction process of performing gain correction on the primary corrected image on the basis of the first gain image to generate a secondary corrected image; a gain-corrected offset difference image generation process of performing gain correction on the offset difference image on the basis of the second gain image to generate a gain-corrected offset difference image; a noise reduction process of performing a low-pass filtering process on the gain-corrected offset difference image; and a tertiary correction process of subtracting the gain-corrected offset difference image subjected to the low-pass filtering process from the secondary corrected image to generate a tertiary corrected image.

Preferably, the processor performs the first offset image acquisition process and the second offset image acquisition process in a state in which gates of the pixels are turned off.

Preferably, the processor performs the noise reduction process on a converted image obtained by performing, on the gain-corrected offset difference image, a multiplication process based on a difference in accumulation time from the radiographic image or an enlargement and reduction process of adjusting an image size to the radiographic image and a process of multiplying a conversion coefficient based on a difference between the reading methods.

According to another aspect of the present disclosure, there is provided a method for operating a radiographic image detection device that includes a pixel region, in which a plurality of pixels that accumulate charge corresponding to radiation emitted from a radiation source to detect the radiation are arranged, and performs radiography, which irradiates the pixel region with the radiation from the radiation source in a state in which a subject is placed between the radiation source and the pixel region and reads a pixel signal corresponding to the charge from the pixel region, to acquire a radiographic image of the subject. The method comprises: a first gain image acquisition step of reading the pixel signal from the pixel region irradiated with the radiation in a state in which the subject is not placed to acquire a first gain image; a pre-irradiation image acquisition step of reading the pixel signal from the pixel region in a state in which the subject is not placed and the radiation is not emitted to acquire a pre-irradiation image; a discarding step of discarding the charge accumulated in the pixels of the pixel region after a dose of the radiation that saturates the charge is emitted in a state in which the subject is not placed; a post-irradiation image acquisition step of reading the pixel signal from the pixel region to acquire a post-irradiation image after the charge is discarded; and a second gain image acquisition step of subtracting the pre-irradiation image from the post-irradiation image to acquire a second gain image.

According to still another aspect of the present disclosure, there is provided an operation program for operating at least one processor included in a radiographic image detection device that includes a pixel region, in which a plurality of pixels that accumulate charge corresponding to radiation emitted from a radiation source to detect the radiation are arranged, and performs radiography, which irradiates the pixel region with the radiation from the radiation source in a state in which a subject is placed between the radiation source and the pixel region and reads a pixel signal corresponding to the charge from the pixel region, to acquire a radiographic image of the subject. The operation program causes the processor to perform: a first gain image acquisition process of reading the pixel signal from the pixel region irradiated with the radiation in a state in which the subject is not placed to acquire a first gain image; a pre-irradiation image acquisition process of reading the pixel signal from the pixel region in a state in which the subject is not placed and the radiation is not emitted to acquire a pre-irradiation image; a discarding process of discarding the charge accumulated in the pixels of the pixel region after a dose of the radiation that saturates the charge is emitted in a state in which the subject is not placed; a post-irradiation image acquisition process of reading the pixel signal from the pixel region to acquire a post-irradiation image after the discarding process is performed; and a second gain image acquisition process of subtracting the pre-irradiation image from the post-irradiation image to acquire a second gain image.

According to the technology of the present disclosure, it is possible to provide a radiographic image detection device that can perform gain correction on an immediately preceding offset image with high accuracy, a method for operating the radiographic image detection device, and a program for operating the radiographic image detection device.

BRIEF DESCRIPTION OF THE DRAWINGS

Exemplary embodiments according to the technique of the present disclosure will be described in detail based on the following figures, wherein.

DETAILED DESCRIPTION

Figure 1:
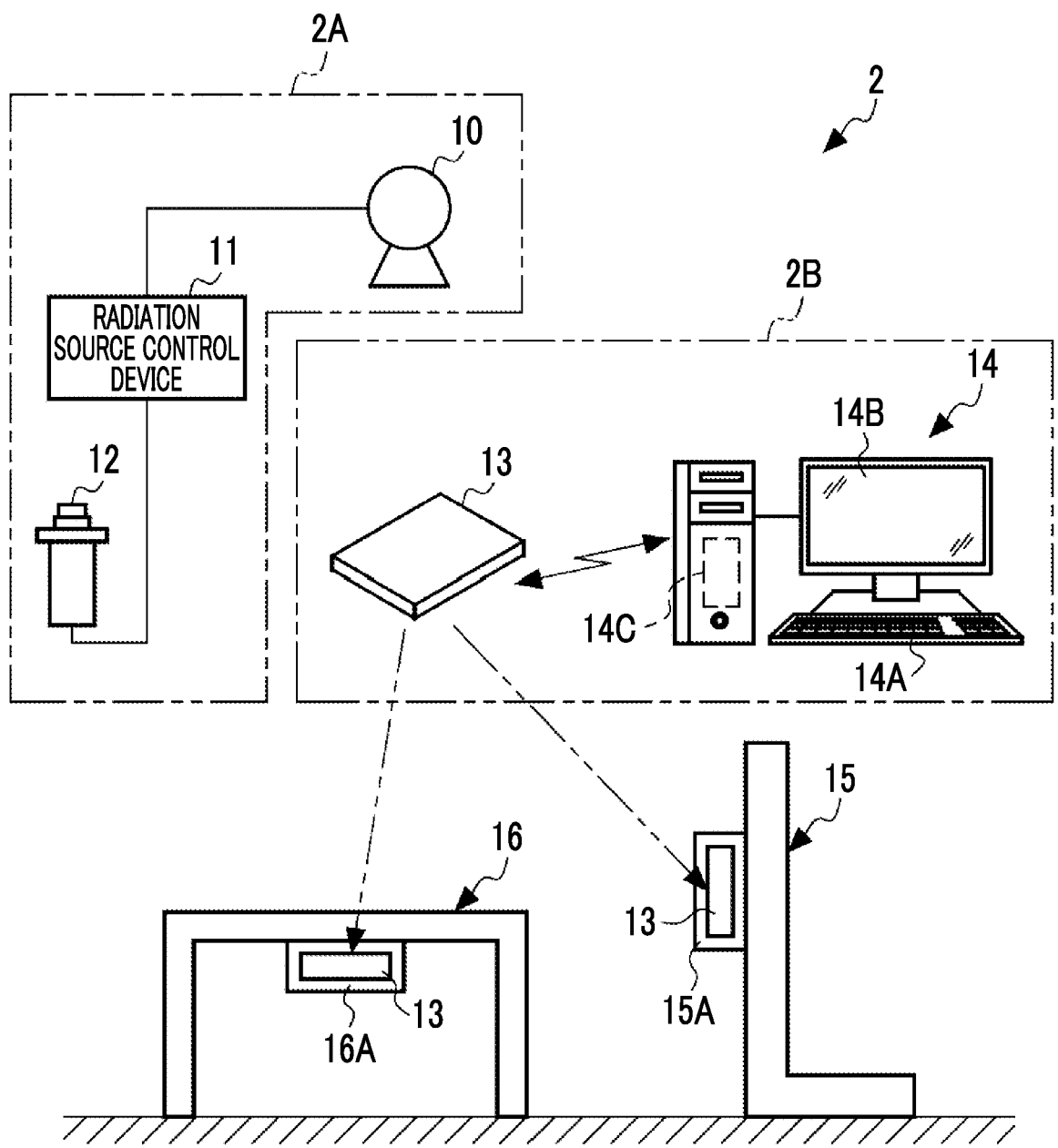
FIG. 1 is a schematic diagram illustrating a configuration of an X-ray imaging system.

In FIG. 1, an X-ray imaging system 2 includes an X-ray generation apparatus 2A and an X-ray imaging apparatus 2B. The X-ray generation apparatus 2A has an X-ray source 10, a radiation source control device 11, and an irradiation switch 12. The radiation source control device 11 controls the operation of the X-ray source 10. The irradiation switch 12 instructs the X-ray source 10 to start warm-up and irradiation with X-rays in response to an operation of an operator such as a radiology technician. In addition, the X-ray is an example of "radiation" according to the technology of the present disclosure.

The X-ray imaging apparatus 2B has an electronic cassette 13 and a console 14. The electronic cassette 13 is a portable X-ray image detection device. The console 14 controls the operation of the electronic cassette 13 and processes the display of an X-ray image. Further, the X-ray imaging system 2 is provided with, for example, an upright imaging stand 15 or a decubitus imaging stand 16. The upright imaging stand 15 is used in a case in which an image of the subject in an upright posture is captured. The decubitus imaging stand 16 is used in a case in which an image of the subject in a decubitus posture is captured. The electronic cassette 13 is set so as to be attachable to and detachable from a holder 15A of the upright imaging stand 15 or a holder 16A of the decubitus imaging stand 16. In addition, the X-ray image is an example of a "radiographic image" according to the technology of the present disclosure. Further, the electronic cassette 13 is an example of a "radiographic image detection device" according to the technology of the present disclosure.

Further, the X-ray imaging system 2 is provided with a radiation source movement device (not illustrated) that is used by the operator to move the X-ray source 10 in a desired direction and position. The radiation source movement device makes it possible to move the X-ray source 10 according to the imaging stand used for X-ray imaging. The operator can move the X-ray source 10 so as to face the upright imaging stand 15 or the decubitus imaging stand 16.

The X-ray generation apparatus 2A and the X-ray imaging apparatus 2B are not electrically connected to each other. That is, the X-ray imaging apparatus 2B is not a synchronous type that operates the electronic cassette 13 in synchronization with the start of irradiation with X-rays, but is an asynchronous type. Therefore, the electronic cassette 13 has an irradiation start detection function of detecting the start of irradiation with X-rays by the X-ray generation apparatus 2A.

As is well known, the X-ray source 10 includes an X-ray tube and an irradiation field limiter (collimator) that limits an irradiation field of X-rays emitted by the X-ray tube. The X-ray tube has a cathode which is a filament emitting thermoelectrons and an anode (target) which collides with the thermoelectrons emitted from the cathode and emits X-rays. In a case in which the X-ray source 10 receives an instruction to start warm-up, it starts preheating the filament and rotating the anode. The warm-up ends in a case in which the preheating of the filament is completed and the anode reaches a prescribed number of rotations.

The console 14 is connected to the electronic cassette 13 by a wired method or a wireless method so as to communicate therewith. The console 14 controls the operation of the electronic cassette 13 in response to an input operation of the operator through an input device 14A such as a keyboard. The X-ray image acquired by the electronic cassette 13 is displayed on a display 14B that is provided in the console 14. In addition, the X-ray image is stored in a storage device 14C, such as a hard disk or a flash memory provided in the console 14, or an image storage server (not illustrated) that is connected to the console 14 by a network.

Figure 2:
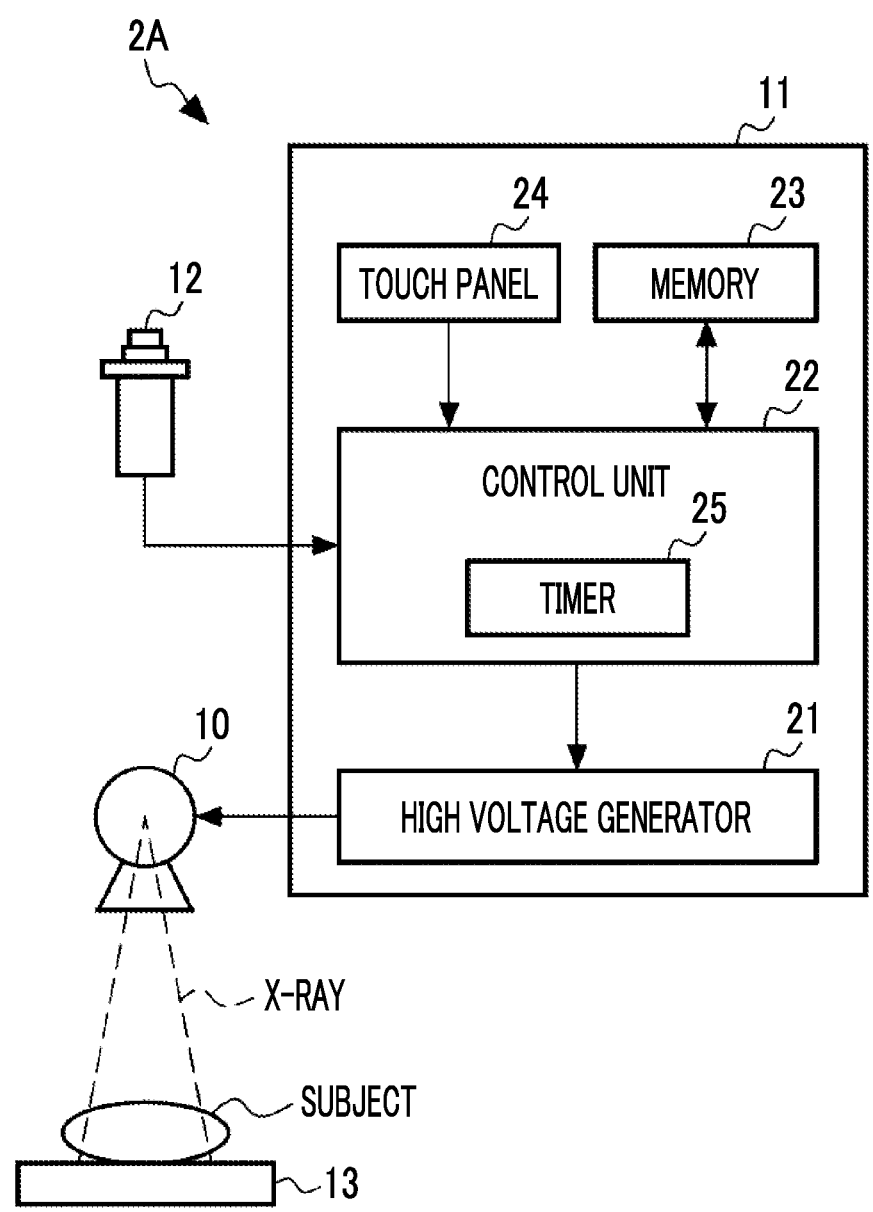
FIG. 2 is a schematic diagram illustrating a configuration of an X-ray generation apparatus.

In FIG. 2, the radiation source control device 11 includes a high voltage generator 21, a control unit 22, a memory 23, and a touch panel 24. The high voltage generator 21 boosts an input voltage with a transformer to generate a high voltage. The high voltage generated by the high voltage generator 21 is supplied as a tube voltage to the X-ray source 10 through a high voltage cable. The control unit 22 controls the tube voltage and a tube current supplied to the X-ray source 10 and an X-ray irradiation time.

The irradiation switch 12, the high voltage generator 21, the memory 23, and the touch panel 24 are connected to the control unit 22. The irradiation switch 12 is a switch that inputs an instruction to the control unit 22. The irradiation switch 12 is configured such that it can be pressed in two steps. In a case in which the irradiation switch 12 is pressed in one step (hereinafter, referred to as "halfway"), the control unit 22 outputs a warm-up instruction signal to the high voltage generator 21 to direct the X-ray source 10 to start warm-up. Further, in a case in which the irradiation switch 12 is pressed in two steps (hereinafter, referred to as "fully"), the control unit 22 outputs an irradiation instruction signal to the high voltage generator 21 to direct the X-ray source 10 to start irradiation with X-rays.

Like the storage device 14C of the console 14, the memory 23 stores in advance several types of imaging conditions including irradiation conditions, such as a tube voltage, a tube current, and an irradiation time. The operator manually sets the imaging conditions through the touch panel 24. A plurality of types of imaging conditions read from the memory 23 are displayed on the touch panel 24. The operator selects the same imaging conditions as the imaging conditions input to the console 14 from the displayed imaging conditions to set the imaging conditions in the radiation source control device 11. The control unit 22 is provided with a timer 25 for stopping the irradiation with X-rays in a case in which the set irradiation time comes.

Figure 3:
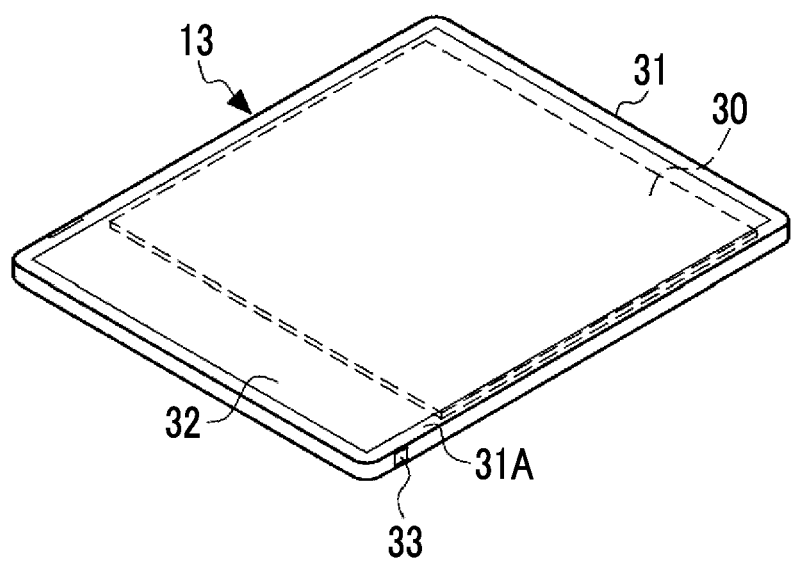
FIG. 3 is a perspective view illustrating an electronic cassette.

In FIG. 3, the electronic cassette 13 is an X-ray image detection device that detects X-rays transmitted through the subject and outputs an X-ray image. The electronic cassette 13 includes an image detection unit 30 and a housing 31. The housing 31 has a flat box shape and accommodates the image detection unit 30. The housing 31 is made of, for example, a conductive resin. In the housing 31, a rectangular opening is formed in a front surface 31A as an incident surface on which X-rays are incident, and an X-ray transmission plate 32 is attached to the opening. The X-ray transmission plate 32 is made of, for example, a carbon material that is lightweight and has high rigidity and high X-ray transparency.

The housing 31 also functions as an electromagnetic shield for preventing electromagnetic noise from entering the electronic cassette 13 and electromagnetic noise from being emitted from the electronic cassette 13 to the outside. In addition, a battery (for example, a secondary battery) that supplies power for driving the electronic cassette 13 and an antenna for performing wireless communication with the console 14 are provided in the housing 31.

For example, the housing 31 has a size conforming to the international standard ISO 4090:2001 which is substantially the same as that of a film cassette or an IP cassette. The electronic cassette 13 is set in the holder 15A of the upright imaging stand 15 or the holder 16A of the decubitus imaging stand 16 so as to be held in a posture in which the front surface 31A of the housing 31 faces the X-ray source 10. In addition, the electronic cassette 13 can be used in a state in which it is placed on the bed on which the subject lies supine, without using the upright imaging stand 15 and the decubitus imaging stand 16.

Figure 4:
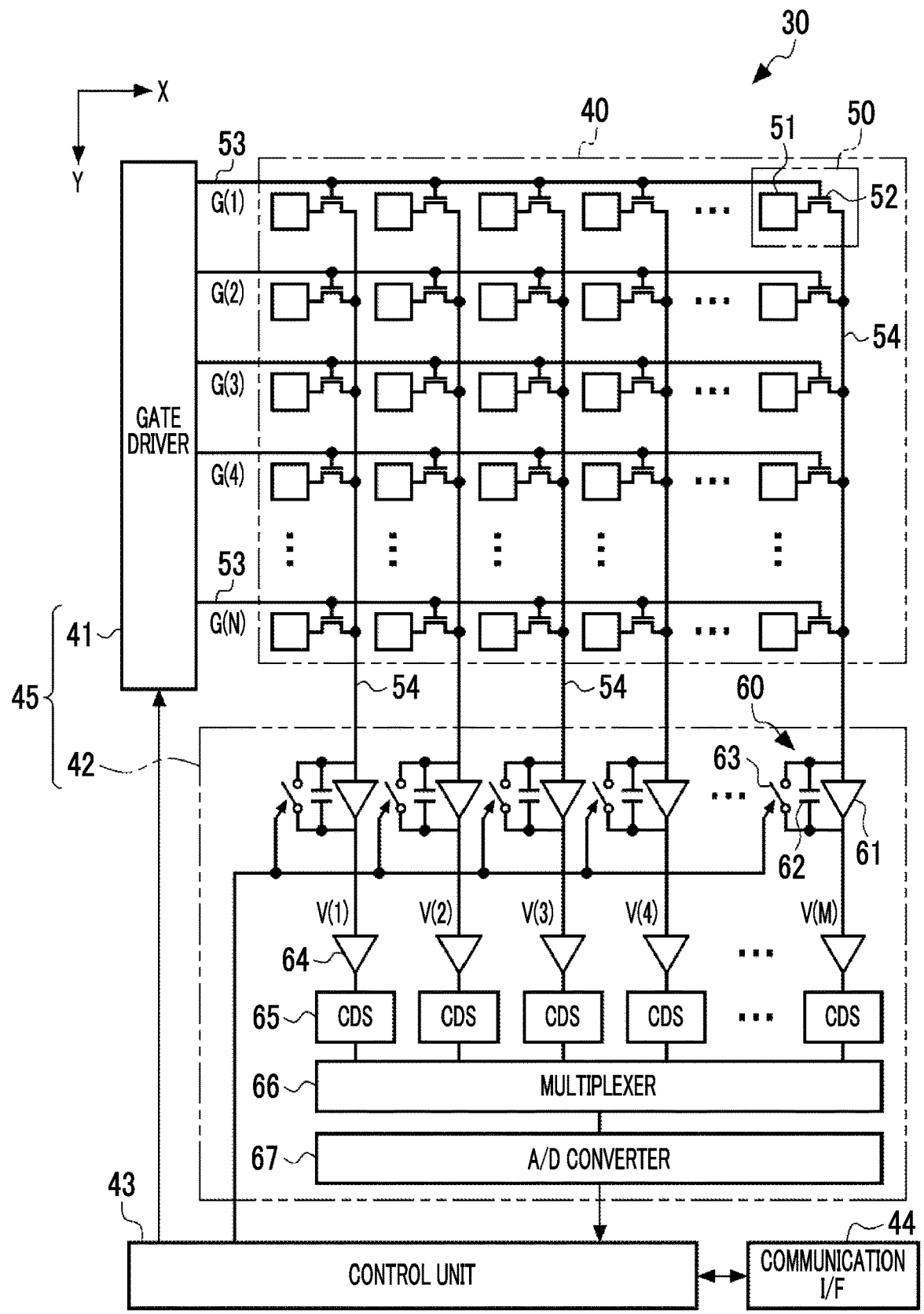
FIG. 4 is a diagram illustrating a configuration of an image detection unit.

In FIG. 4, the image detection unit 30 includes a pixel region 40, a gate driver 41, a signal processing circuit 42, a control unit 43, and a communication interface (I/F) 44. The gate driver 41 and the signal processing circuit 42 form a reading unit 45 that reads a pixel signal from the pixel region 40. The gate driver 41 and the signal processing circuit 42 are an example of a "reading unit" according to the technology of the present disclosure.

The pixel region 40 is formed on a thin film transistor (TFT) active matrix substrate. The pixel region 40 includes a plurality of pixels 50 that are arranged in a matrix along the X direction and the Y direction which are orthogonal to each other. It is assumed that the number of pixels 50 arranged in the X direction is M and the number of pixels 50 arranged in the Y direction is N. Each of N and M is an integer that is equal to or greater than 2. For example, each of N and M is about 2000. The array pattern of the pixels 50 is not limited to a square array, and may be a non-square array such as a so-called honeycomb array. The pixel 50 is an element that generates and accumulates charge according to the amount of incident X-rays.

The pixel region 40 is provided with a scintillator (not illustrated) that converts X-rays into visible light. The image detection unit 30 is an indirect conversion type in which photoelectric conversion is performed on the visible light converted by the scintillator in each pixel 50. The scintillator is made of, for example, CsI:Tl (thallium-activated cesium iodide) or $Gd_2O_2S$:Tb (terbium-activated gadolinium oxysulfide) and is disposed so as to face the entire surface of the pixel region 40. The image detection unit 30 is, for example, a penetration side sampling (PSS) type in which the scintillator and the TFT active matrix substrate are disposed in this order from an X-ray incident side. Further, the image detection unit 30 may be an irradiation side sampling (ISS) type in which the TFT active matrix substrate and the scintillator are disposed in this order from the X-ray incident side.

The image detection unit 30 is not limited to the indirect conversion type, but may be a direct conversion type using a conversion layer (for example, amorphous selenium) that directly converts X-rays into charge.

The pixel 50 includes a photoelectric conversion unit 51 that performs photoelectric conversion on the visible light converted by the scintillator to generate charge and accumulates the charge and a TFT 52 as a switching element. The photoelectric conversion unit 51 includes, for example, a p-intrinsic-n (PIN) semiconductor layer, an upper electrode that is disposed above the semiconductor layer, and a lower electrode that is disposed below the semiconductor layer. A bias voltage is applied to the upper electrode. The lower electrode is connected to the TFT 52.

The pixel region 40 includes N scanning lines 53 that extend in the X direction and M signal lines 54 that extend in the Y direction. The N scanning lines 53 and the M signal lines 54 are wired in a grid shape. Each pixel 50 is connected to an intersection portion of the scanning line 53 and the signal line 54. Specifically, in the pixel 50, a gate electrode of the TFT 52 is connected to the scanning line 53 and a source electrode of the TFT 52 is connected to the signal line 54. A drain electrode of the TFT 52 is connected to the photoelectric conversion unit 51.

Each scanning line 53 is commonly connected to M pixels 50 corresponding to one pixel row. Each signal line 54 is commonly connected to N pixels 50 corresponding to one pixel column. Each scanning line 53 is connected to the gate driver 41. Each signal line 54 is connected to the signal processing circuit 42.

The gate driver 41 outputs a gate pulse G(n) as a scanning signal to an n-th scanning line 53. Here, n is an integer from 1 to N. The gate pulse G(n) is applied to the gate electrodes of the TFTs 52 connected to the n-th scanning line 53. The TFT 52 is turned on in a case in which the voltage of the gate pulse G(n) is at a high level and is turned off in a case in which the voltage is at a low level. The time when the TFT 52 is turned on is defined by the width of the gate pulse G(n).

The charge accumulated in the photoelectric conversion unit 51 of the pixel 50 is output to the signal processing circuit 42 through the signal line 54 in a case in which the TFT 52 is turned on.

The signal processing circuit 42 includes an integrator 60 as a charge amplifier, an amplifier 64, a correlated double sampling (CDS) circuit 65, a multiplexer 66, and an analog/digital (A/D) converter 67. The integrator 60 is individually connected to each signal line 54. Each integrator 60 includes an operational amplifier 61, a capacitor 62, and a reset switch 63. The capacitor 62 and the reset switch 63 are connected in parallel between an input terminal and an output terminal of the operational amplifier 61. The signal line 54 is connected to the input terminal of the operational amplifier 61.

The integrator 60 integrates the charge input from the signal line 54, converts an integrated value into an analog voltage signal V(k), and outputs the analog voltage signal V(k). Here, k is an integer from 1 to M. The analog voltage signal V(k) corresponds to the integrated value of the charge input from a k-th signal line 54 to the integrator 60.

The output terminal of the operational amplifier 61 of each pixel column is connected to the input side of the multiplexer 66 through the amplifier 64 and the CDS circuit 65. The A/D converter 67 is connected to the output side of the multiplexer 66. The CDS circuit 65 has a sample-and-hold circuit. The CDS circuit 65 performs correlated double sampling on the analog voltage signal V(k) to remove a reset noise component.

The multiplexer 66 sequentially selects the connected M CDS circuits 65 and sequentially inputs the analog voltage signal V(k) subjected to the correlated double sampling to the A/D converter 67. In addition, the amplifier 64 is not limited to the configuration in which it is provided between the integrator 60 and the CDS circuit 65, but may be provided between the CDS circuit 65 and the A/D converter 67.

The A/D converter 67 sequentially converts the analog voltage signal V(k) input from the multiplexer 66 into a digital value and outputs the digital value as a pixel signal to the control unit 43. That is, the pixel signal is a signal corresponding to the amount of incident X-rays read from the pixel region 40 by the reading unit 45. The pixel signals corresponding to one frame which have been read from each pixel 50 of the pixel region 40 form an X-ray image.

The control unit 43 controls the operation of the reading unit 45 reading the pixel signal from the pixel region 40 to perform an X-ray imaging process, and performs a process of generating an X-ray image based on the read pixel signal. Further, the control unit 43 performs a calibration process of acquiring an offset image in a state in which no X-rays are emitted and a correction process of correcting the X-ray image on the basis of the acquired offset image, which will be described in detail below. Furthermore, the control unit 43 performs the above-mentioned irradiation start detection process.

The communication I/F 44 is connected to the console 14 (see FIG. 1) wirelessly or in a wired manner, and transmits and receives data to and from the console 14. For example, the communication I/F 44 receives data including imaging conditions transmitted from the console 14 and transmits data indicating the X-ray image generated by the control unit 43 to the console 14. The imaging conditions include the irradiation time determined corresponding to, for example, an imaging part.

Figure 5:
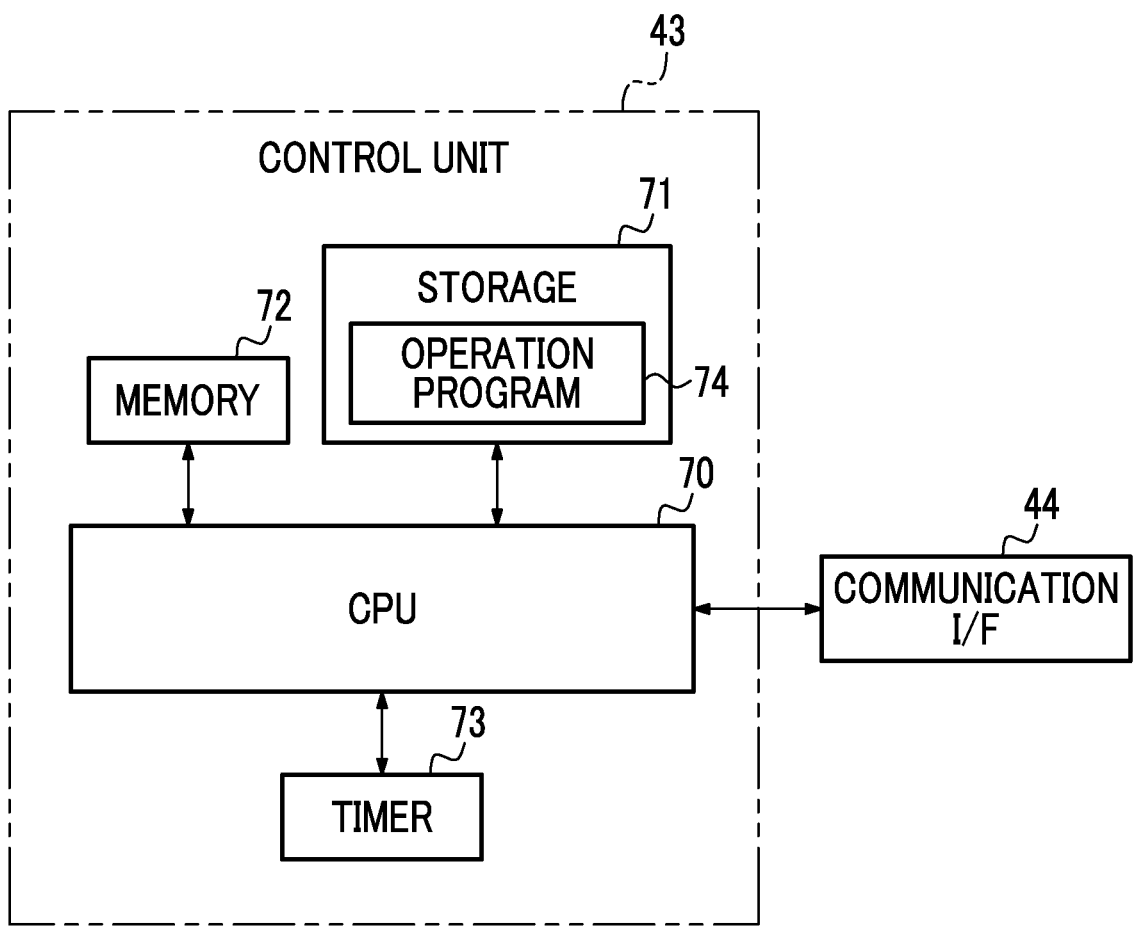
FIG. 5 is a block diagram illustrating a configuration of a control unit.

In FIG. 5, the control unit 43 of the image detection unit 30 includes, for example, a central processing unit (CPU) 70, a storage 71, a memory 72, and a timer 73. The storage 71 stores an operation program 74 and various kinds of data. The storage 71 is a non-volatile storage device such as a flash memory. The memory 72 is a volatile storage device, such as a random access memory (RAM) and is used as a work memory. The timer 73 is a timing device that measures time such as the irradiation time. The CPU 70 operates each unit on the basis of the operation program 74 to implement various functions. The CPU 70 is an example of a "processor" according to the technology of the present disclosure.

Figure 6:
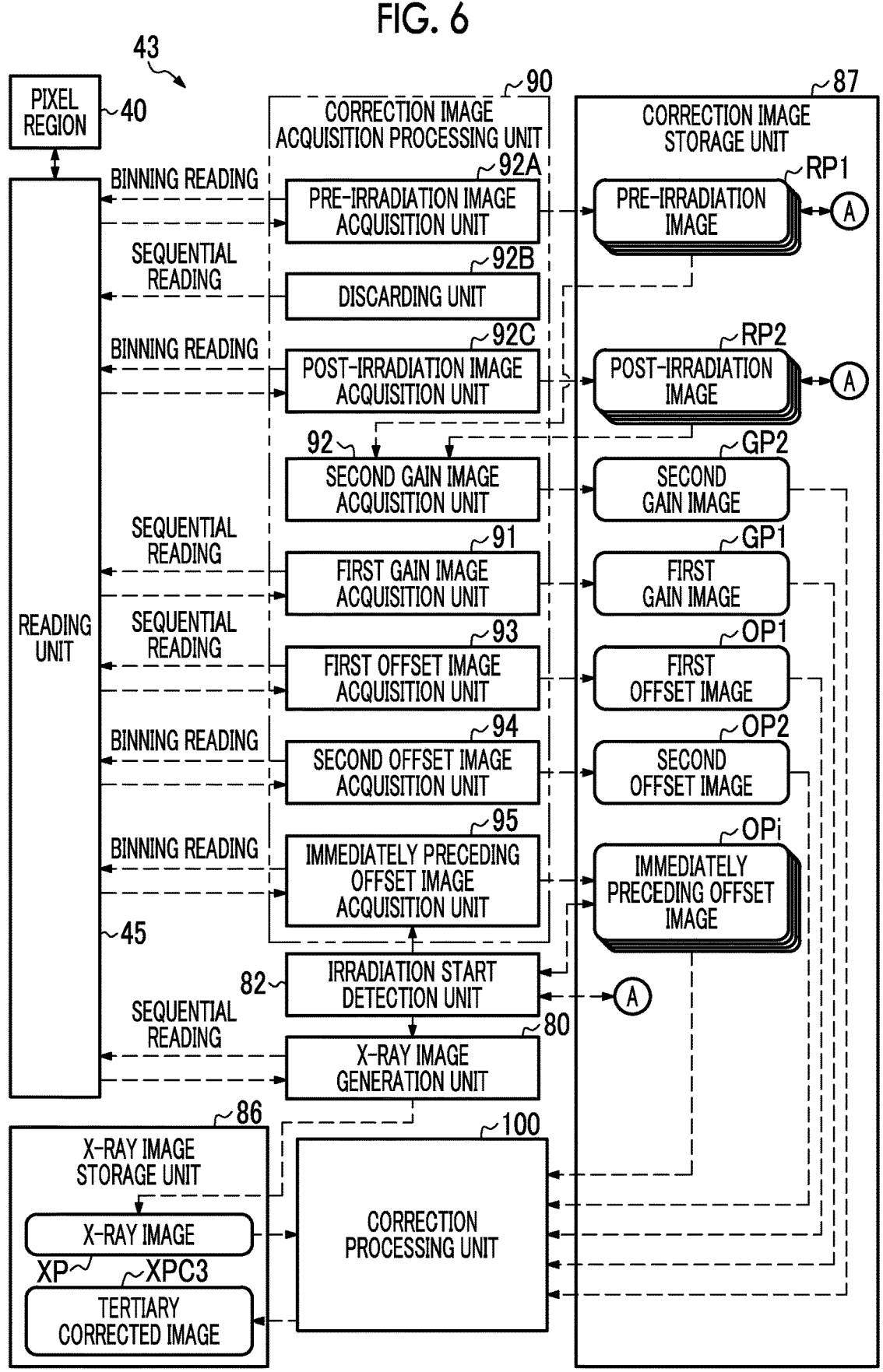
FIG. 6 is a block diagram illustrating functions implemented by the control unit.

FIG. 6 illustrates various functional units that are implemented in the control unit 43 by the CPU 70. In FIG. 6, an X-ray image generation unit 80, an irradiation start detection unit 82, a correction image acquisition processing unit 90, and a correction processing unit 100 are implemented in the control unit 43. The correction image acquisition processing unit 90 includes a first gain image acquisition unit 91, a pre-irradiation image acquisition unit 92A, a discarding unit 92B, a post-irradiation image acquisition unit 92C, a second gain image acquisition unit 92, a first offset image acquisition unit 93, a second offset image acquisition unit 94, and an immediately preceding offset image acquisition unit 95. In addition, each of an X-ray image storage unit 86 and a correction image storage unit 87 is implemented using the storage 71 and/or the memory 72.

Figure 7:
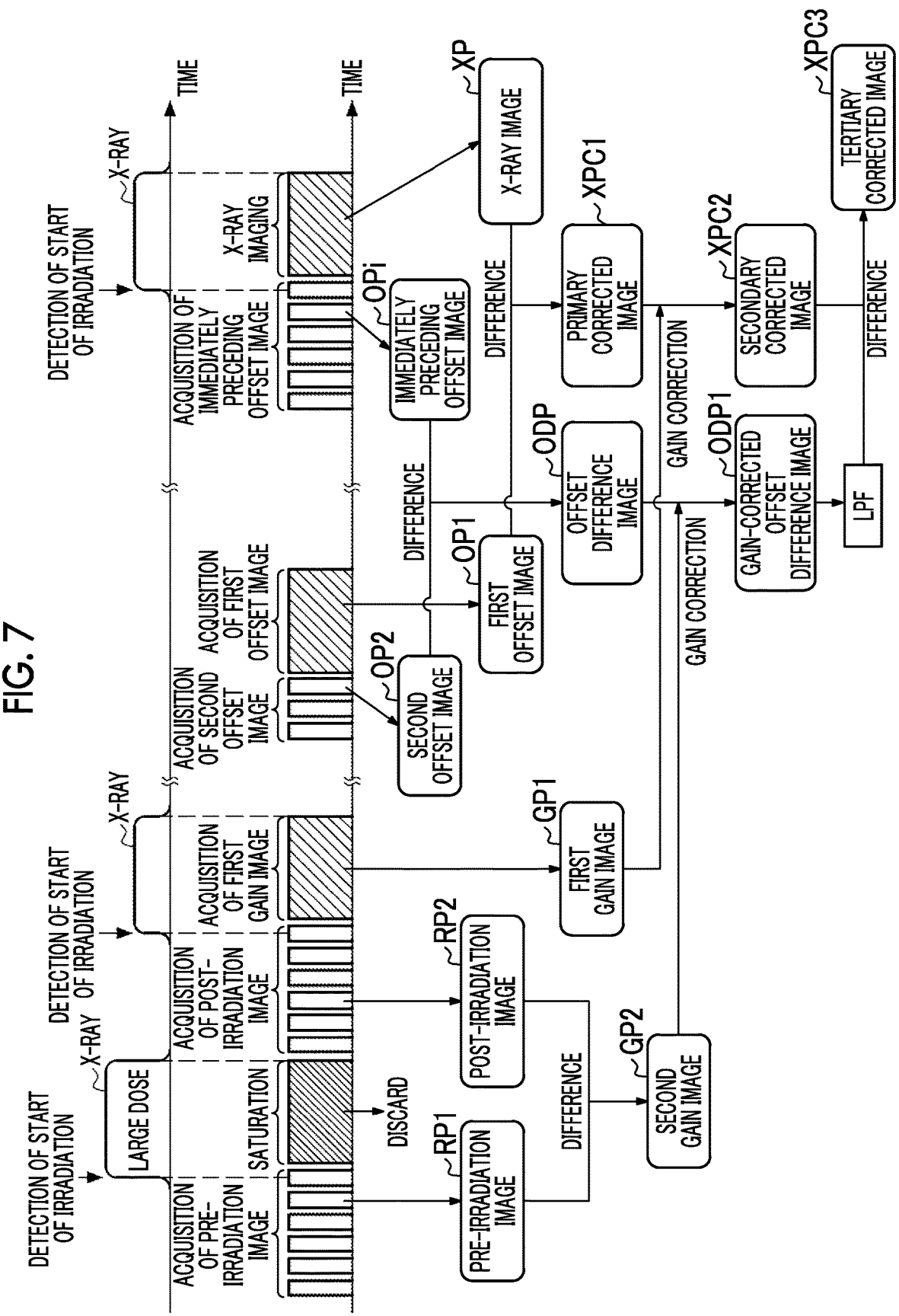
FIG. 7 is a schematic diagram illustrating the outline of a process performed by the control unit.

As illustrated in FIG. 7, the X-ray image generation unit 80 operates during X-ray imaging that is performed in a state in which X-rays are emitted. After the pixel region 40 is irradiated with the X-rays generated by the X-ray generation apparatus 2A through the subject, the X-ray image generation unit 80 drives the reading unit 45 to read pixel signals from the pixel region 40. Then, the X-ray image generation unit 80 generates an X-ray image XP on the basis of the read pixel signals. That is, the X-ray image generation unit 80 performs an X-ray image generation process.

Figure 8:
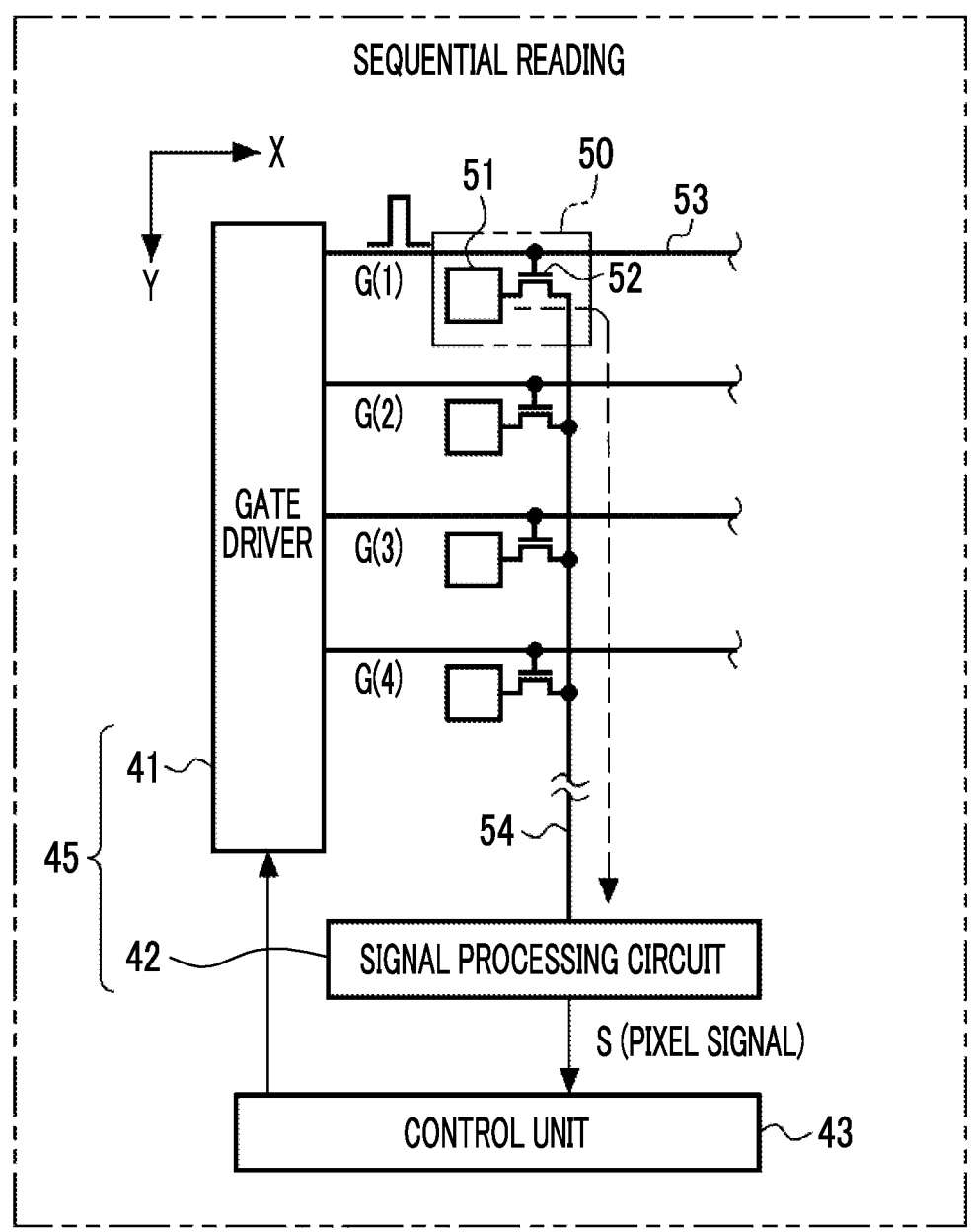
FIG. 8 is a diagram illustrating a sequential reading method.

The X-ray image generation unit 80 drives the reading unit 45 using a "sequential reading method" which sequentially selects the scanning lines 53 and individually reads the charge accumulated in each pixel 50 included in the pixel region 40. As illustrated in FIG. 8, in the sequential reading method, the gate driver 41 sequentially applies the gate pulse to the N scanning lines 53 to sequentially select the scanning lines 53 and reads charge from the pixels 50 connected to the selected scanning line 53.

In the sequential reading method, the TFTs 52 connected to one scanning line 53, to which the gate pulse has been applied, are turned on, and charge is output from the photoelectric conversion units 51 connected to the TFTs 52 to the signal line 54. The charge output to the signal line 54 is subjected to signal processing by the signal processing circuit 42 and is input as a pixel signal S to the control unit 43. The X-ray image generation unit 80 generates the X-ray image XP on the basis of the pixel signals S corresponding to all of the pixels 50 included in the pixel region 40. The X-ray image generation unit 80 stores the generated X-ray image XP in the X-ray image storage unit 86.

As illustrated in FIG. 7, the immediately preceding offset image acquisition unit 95 included in the correction image acquisition processing unit 90 operates immediately before the X-ray imaging. The immediately preceding offset image acquisition unit 95 drives the reading unit 45 in a state in which the pixel region 40 is not irradiated with the X-rays immediately before the X-ray imaging to read the pixel signals from the pixel region 40. Then, the immediately preceding offset image acquisition unit 95 generates an immediately preceding offset image OPi on the basis of the read pixel signals. That is, the immediately preceding offset image acquisition unit 95 performs an immediately preceding offset image acquisition process. In addition, the immediately preceding offset image acquisition unit 95 repeatedly performs the immediately preceding offset image acquisition process a plurality of times to acquire a plurality of immediately preceding offset images OPi immediately before the X-ray imaging. The immediately preceding offset image acquisition unit 95 stores the plurality of acquired immediately preceding offset images OPi in the correction image storage unit 87.

Figure 9:
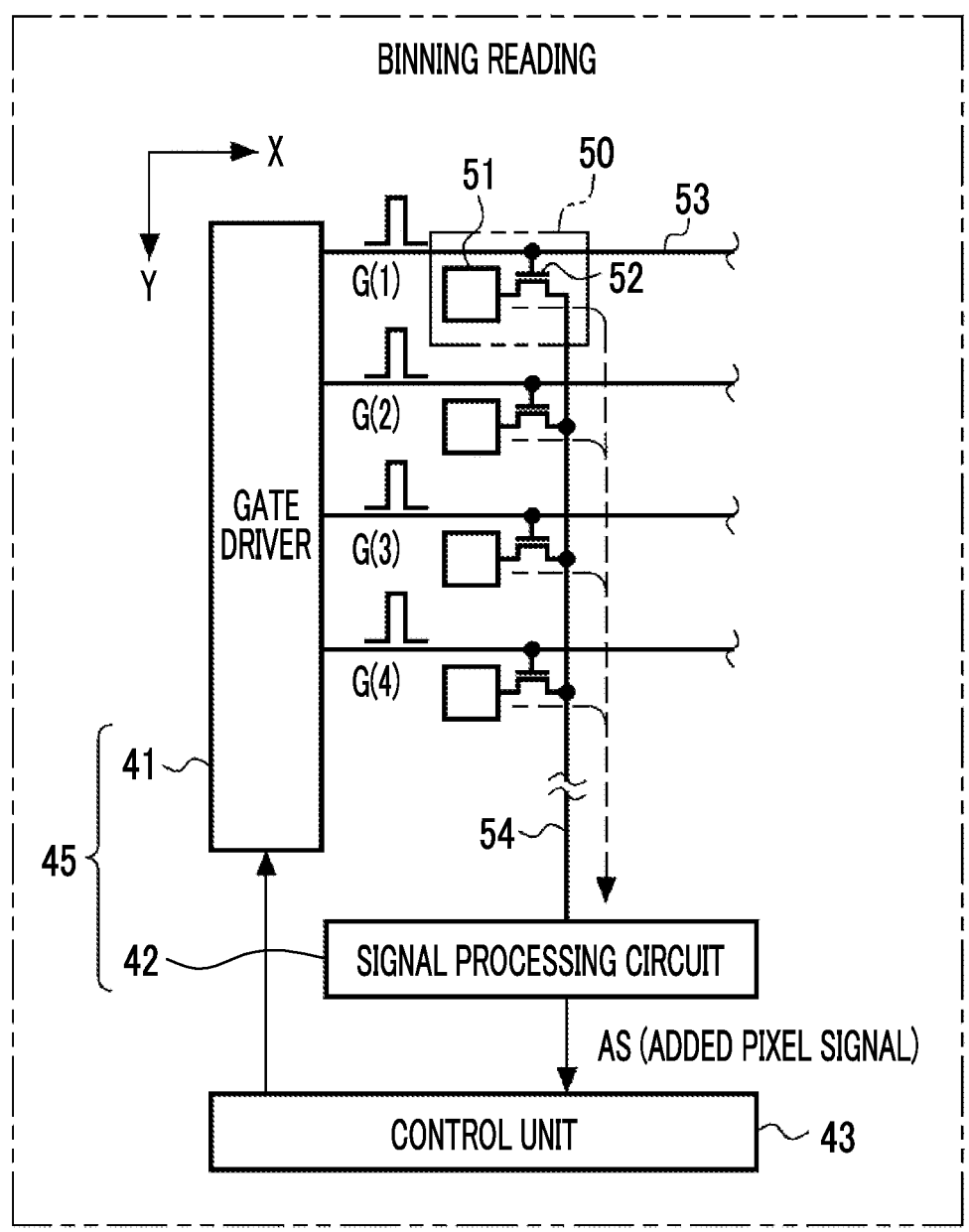
FIG. 9 is a diagram illustrating a binning reading method.

The immediately preceding offset image acquisition unit 95 drives the reading unit 45 using a "binning reading method" that simultaneously selects a plurality of scanning lines 53 adjacent to each other, adds charge accumulated in a plurality of pixels 50 included in the pixel region 40, and reads the added charge. As illustrated in FIG. 9, in the binning reading method, the N scanning lines 53 are divided into sets of four scanning lines 53, and the gate driver 41 simultaneously applies the gate pulse to each set of four scanning lines 53, adds charge corresponding to four pixels, and reads the added charge. In addition, the number of pixels added by the binning reading is not limited to four pixels.

In the binning reading method, the TFTs 52 connected to the plurality of scanning lines 53, to which the gate pulses have been applied, are turned on, and charge is output from the photoelectric conversion units 51 connected to the TFTs 52 to the signal lines 54. A plurality of charges output from a plurality of pixels 50 connected to the same signal line 54 are added on the signal line 54 and are then input to the signal processing circuit 42. The charge input to the signal processing circuit 42 is subjected to signal processing and is input as an added pixel signal AS to the control unit 43. The immediately preceding offset image acquisition unit 95 generates the immediately preceding offset image OPi on the basis of the added pixel signal AS corresponding to each addition pixel included in the pixel region 40. In addition, the addition pixels indicate a plurality of pixels 50 from which charge is added. In this embodiment, as illustrated in FIG. 9, four pixels 50 arranged in the Y direction are the addition pixels.

Figure 10:
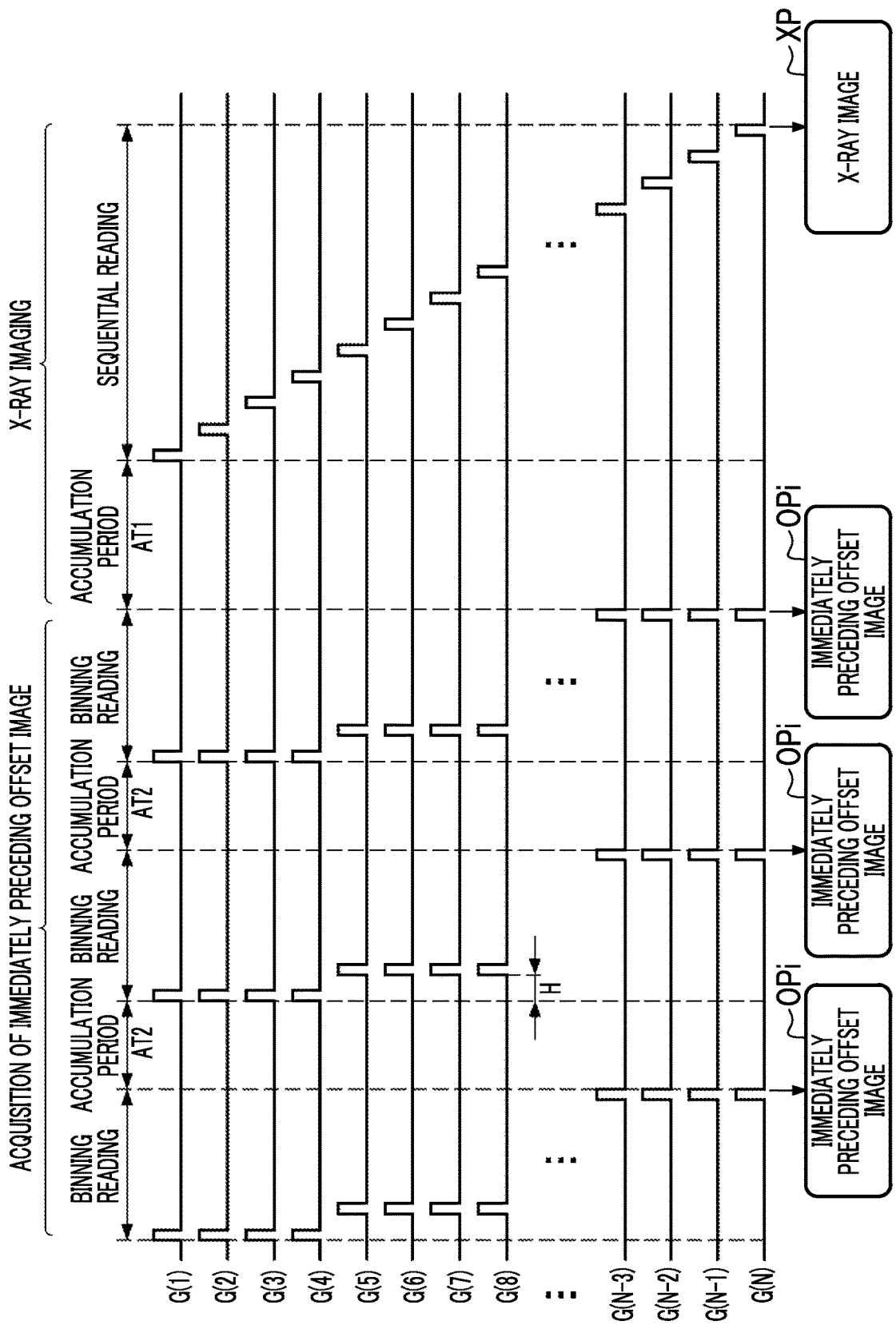
FIG. 10 is a timing chart illustrating the timing of gate pulses during X-ray imaging.

As illustrated in FIG. 10, in the sequential reading performed during the X-ray imaging, the scanning lines 53 are sequentially selected one by one. In contrast, in the binning reading performed during the acquisition of the immediately preceding offset image, the scanning lines 53 are sequentially selected four by four. Therefore, in this embodiment, the read time in the binning reading method is about one fourth of the read time in the sequential reading method.

Further, since the operation of the immediately preceding offset image acquisition unit 95 acquiring the immediately preceding offset image OPi is performed immediately before the X-ray imaging, it also functions as a reset operation of discarding the charge accumulated in the pixel region 40 immediately before the X-ray imaging. Therefore, a charge accumulation period (hereinafter, simply referred to as an "accumulation period") AT1 in the X-ray imaging corresponds to a period from the end of the binning reading immediately before the X-ray imaging to the start of the sequential reading. During the accumulation period AT1, charge corresponding to the amount of X-rays emitted is mainly accumulated in the pixel region 40.

In the operation of acquiring the immediately preceding offset image OPi, the binning reading is periodically repeated. Therefore, an accumulation period AT2 in the operation of acquiring the immediately preceding offset image OPi corresponds to a period from the end of the binning reading to the start of the next binning reading. During the accumulation period AT2, the charge caused by the dark current generated in each pixel 50 is mainly accumulated in the pixel region 40. The dark current is a noise component that is generated in a state in which no X-rays are emitted and is mainly caused by heat. In addition, during the accumulation period AT1, in addition to the charge corresponding to the amount of X-rays emitted, the charge caused by the dark current is accumulated in the pixel region 40.

The accumulation period AT2 may have the same length as the accumulation period AT1. However, in this embodiment, the accumulation period AT2 is set to be shorter than the accumulation period AT1 in order to shorten the acquisition time of the immediately preceding offset image OPi (that is, AT2<AT1). In this embodiment, since the pixel signal is read by the binning reading method during the operation of acquiring the immediately preceding offset image OPi, the immediately preceding offset image OPi can be acquired in a shorter time than the X-ray image XP. Furthermore, since AT2<AT1 is satisfied, the immediately preceding offset image OPi can be acquired in a shorter time.

Figure 11:
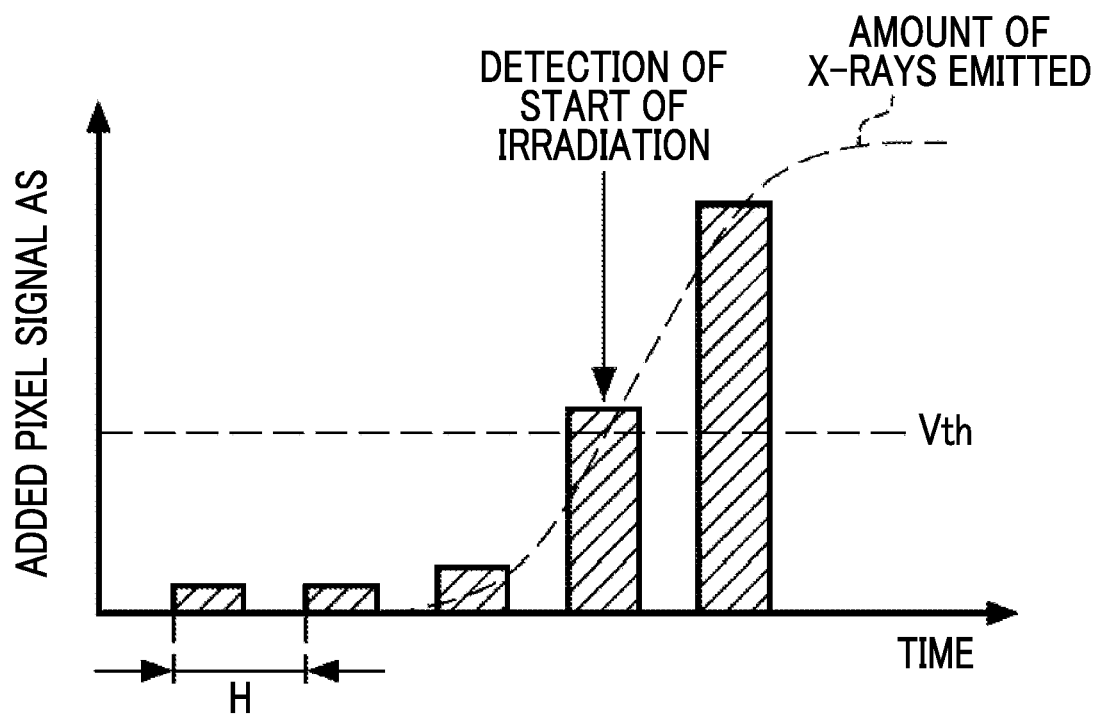
FIG. 11 is a diagram illustrating an irradiation start determination process.

Returning to FIG. 6, the irradiation start detection unit 82 detects that the X-ray generation apparatus 2A has started irradiation with X-rays on the basis of the immediately preceding offset image OPi acquired by the immediately preceding offset image acquisition unit 95. Specifically, the irradiation start detection unit 82 monitors the signal value of the added pixel signal AS read by the binning reading in the operation of acquiring the immediately preceding offset image OPi, as illustrated in FIG. 11. The irradiation start detection unit 82 determines that irradiation with X-rays has been started in a case in which the signal value of the added pixel signal AS is equal to or greater than a threshold value Vth. For example, the irradiation start detection unit 82 performs irradiation start detection every selection switching time H of the scanning line 53 (see FIG. 10). The selection switching time H is the time interval of the gate pulse output from the gate driver 41.

For example, the irradiation start detection unit 82 performs the irradiation start detection on the basis of the added pixel signal AS obtained through one signal line 54. In addition, the irradiation start detection unit 82 may perform the irradiation start detection on the basis of the maximum value of the added pixel signals AS obtained through a plurality of signal lines 54 for each pixel row. Further, the irradiation start detection unit 82 may perform the irradiation start detection on the basis of an average value or a sum, instead of the maximum value of the added pixel signals AS for each pixel row. Furthermore, the irradiation start detection unit 82 may perform the irradiation start detection on the basis of a difference value between the added pixel signals AS acquired every selection switching time H.

In a case in which the start of irradiation with X-rays has been detected, the irradiation start detection unit 82 notifies the immediately preceding offset image acquisition unit 95 and the X-ray image generation unit 80 that the start of irradiation has been detected. In a case in which the notification is received from the irradiation start detection unit 82, the immediately preceding offset image acquisition unit 95 stops the binning reading after the binning reading is performed on the final scanning line 53. In a case in which the notification is received from the irradiation start detection unit 82, the X-ray image generation unit 80 starts the measurement of the irradiation time from the time when the binning reading is stopped with the timer 73 (see FIG. 5). The irradiation time is a value that is included in the imaging conditions acquired by the control unit 43 from the console 14. The X-ray image generation unit 80 starts the sequential reading in a case in which the irradiation time has elapsed. The irradiation period corresponds to the accumulation period AT1.

The first gain image acquisition unit 91 performs a gain calibration process of acquiring a first gain image GP1, for example, during the maintenance of the X-ray imaging system 2. As illustrated in FIG. 7, the first gain image GP1 is acquired before the X-ray imaging and the acquisition of the immediately preceding offset image OPi.

The first gain image acquisition unit 91 drives the reading unit 45 using the same reading method (that is, the sequential reading method) as the X-ray image generation unit 80 except that irradiation with X-rays is performed in a state in which no subject is placed. The first gain image acquisition unit 91 performs a first gain image acquisition process of reading the pixel signal S from the pixel region 40, which has been irradiated with the X-rays, to acquire the first gain image GP1. The irradiation with X-rays in a case in which the first gain image GP1 is acquired is performed under the same imaging conditions as the irradiation with X-rays in a case in which the X-ray image generation unit 80 generates the X-ray image XP.

The first gain image GP1 is an image including sensitivity difference information indicating a difference in the sensitivity of each pixel 50 to the X-rays since it is acquired in a state in which no subject is placed.

A second gain image GP2 is acquired during the gain calibration process in a state in which no subject is placed. The second gain image GP2 is acquired by operating the pre-irradiation image acquisition unit 92A, the discarding unit 92B, the post-irradiation image acquisition unit 92C, and the second gain image acquisition unit 92. The acquired second gain image GP2 is stored in the correction image storage unit 87. In this embodiment, the second gain image GP2 is acquired before the first gain image GP1 is acquired. However, the second gain image GP2 may be acquired after the first gain image GP1 is acquired.

In a case in which the second gain image GP2 is acquired, the radiation source control device 11 directs the X-ray source 10 to irradiate the electronic cassette 13 with such a large dose of X-rays that the charge accumulated in all of the pixels 50 included in the pixel region 40 is saturated.

The pre-irradiation image acquisition unit 92A drives the reading unit 45 using the same reading method (that is, the binning reading method) as the immediately preceding offset image acquisition unit 95. The pre-irradiation image acquisition unit 92A performs a pre-irradiation image acquisition process of reading the added pixel signal AS from the pixel region 40, which has not been irradiated with X-rays, to acquire a pre-irradiation image RP1.

The pre-irradiation image acquisition unit 92A operates immediately before irradiation with a large dose of X-rays. The pre-irradiation image acquisition unit 92A repeatedly performs the pre-irradiation image acquisition process to acquire a plurality of pre-irradiation images RP1, similarly to the immediately preceding offset image acquisition unit 95. The pre-irradiation image acquisition unit 92A stores the acquired pre-irradiation images RP1 in the correction image storage unit 87.

The discarding unit 92B performs a discarding process of discarding the charge accumulated in each pixel 50 of the pixel region 40 after the irradiation with a large dose of X-rays is performed. For example, the discarding unit 92B drives the reading unit 45 using the sequential reading method to read the pixel signal S from the pixel region 40 and discards the read pixel signal S. In addition, the discarding unit 92B drives the reading unit 45 using the binning reading method to read the added pixel signal AS from the pixel region 40 and discards the read added pixel signal AS.

The post-irradiation image acquisition unit 92C drives the reading unit 45 using the same reading method (that is, the binning reading method) as the immediately preceding offset image acquisition unit 95. The post-irradiation image acquisition unit 92C performs a post-irradiation image acquisition process of reading the added pixel signal AS from the pixel region 40, which has not been irradiated with X-rays, to acquire a post-irradiation image RP2.

The post-irradiation image acquisition unit 92C operates immediately after the discarding unit 92B performs the discarding process. The post-irradiation image acquisition unit 92C repeatedly performs the post-irradiation image acquisition process to acquire a plurality of post-irradiation images RP2, similarly to the immediately preceding offset image acquisition unit 95. The post-irradiation image acquisition unit 92C stores the acquired post-irradiation images RP2 in the correction image storage unit 87.

The second gain image acquisition unit 92 performs a second gain image acquisition process of acquiring one pre-irradiation image RP1 and one post-irradiation image RP2 from the correction image storage unit 87 and subtracting the pre-irradiation image RP1 from the post-irradiation image RP2 to acquire the second gain image GP2. In addition, since the pre-irradiation image RP1 and the post-irradiation image RP2 acquired most immediately before the start of irradiation with X-rays are affected by the irradiation with X-rays, the second gain image acquisition unit 92 acquires the pre-irradiation image RP1 and the post-irradiation image RP2 other than most immediately before the start of irradiation with X-rays. The second gain image acquisition unit 92 stores the acquired second gain image GP2 in the correction image storage unit 87.

The pre-irradiation image RP1 is an image including the same noise component as the immediately preceding offset image OPi. The pre-irradiation image RP1 and the immediately preceding offset image OPi mainly include dark current noise (DCN) generated in the pixel 50 and fixed pattern noise (FPN). The DCN is mainly caused by a dark current that is generated in each pixel 50 due to heat. The FPN is mainly caused by a variation in the characteristics of the integrator 60 connected to each signal line 54. Since the DCN is caused by heat, it varies due to a temperature change. In contrast, since the FPN is caused by the characteristics of the integrator 60, it is constant regardless of a temperature change.

The post-irradiation image RP2 is an image acquired in a state in which the pixel region 40 is irradiated with such a large dose of X-rays that the accumulated charge is saturated and the charge is discarded. That is, the post-irradiation image RP2 is an image acquired in a state in which a dark current caused by a residual charge (that is, a residual image) in, for example, the TFT 52 of each pixel 50 flows to each signal line 54. In the residual image, a variation is small between the pixels. Therefore, the post-irradiation image RP2 does not include the sensitivity difference information indicating the difference in the sensitivity of each pixel 50 to X-rays. Therefore, unlike the first gain image GP1, the post-irradiation image RP2 is an image that mainly includes a large amount of high frequency noise generated by the flow of the dark current from the pixel region 40 to the reading unit 45.

Therefore, the second gain image GP2 obtained by subtracting the pre-irradiation image RP1 from the post-irradiation image RP2 mainly includes high frequency noise caused by the dark current due to the residual image. The use of the second gain image GP2 makes it possible to perform gain correction on the immediately preceding offset image OPi with high accuracy.

The irradiation start detection unit 82 also operates during the gain calibration process. The irradiation start detection unit 82 detects whether or not the X-ray generation apparatus 2A has started irradiation with a large dose of X-rays on the basis of the pre-irradiation image RP1 acquired by the pre-irradiation image acquisition unit 92A. In a case in which the start of the irradiation with X-rays has been detected, the irradiation start detection unit 82 notifies the pre-irradiation image acquisition unit 92A and the discarding unit 92B that the start of irradiation has been detected. In a case in which the notification is received from the irradiation start detection unit 82, the pre-irradiation image acquisition unit 92A stops the reading operation. After the irradiation time has elapsed since the reception of the notification from the irradiation start detection unit 82, the discarding unit 92B reads the pixel signal S to perform the charge discarding process.

In addition, the irradiation start detection unit 82 detects whether or not the X-ray generation apparatus 2A has started irradiation with X-rays on the basis of the post-irradiation image RP2 acquired by the post-irradiation image acquisition unit 92C after the discarding process of the discarding unit 92B. In a case in which the start of the irradiation with X-rays has been detected, the irradiation start detection unit 82 notifies the post-irradiation image acquisition unit 92C and the first gain image acquisition unit 91 that the start of irradiation has been detected. In a case in which the notification is received from the irradiation start detection unit 82, the post-irradiation image acquisition unit 92C stops the reading operation. After the irradiation time has elapsed since the reception of the notification from the irradiation start detection unit 82, the first gain image acquisition unit 91 reads the pixel signal S to acquire the first gain image GP1.

A specific detection process of the irradiation start detection unit 82 during the gain calibration process is the same as the detection process during the X-ray imaging (see FIG. 11).

For example, the first offset image acquisition unit 93 and the second offset image acquisition unit 94 perform an offset calibration process in a case in which the electronic cassette 13 is started up. As illustrated in FIG. 7, the first offset image OP1 and the second offset image OP2 are acquired before the X-ray imaging and the acquisition of the immediately preceding offset image OPi. For example, calibration is automatically performed in a case in which the electronic cassette 13 is started up, regardless of the operation of the operator. In addition, the calibration may be performed according to the operation of the operator.

The first offset image acquisition unit 93 drives the reading unit 45 using the same reading method (that is, the sequential reading method) as the X-ray image generation unit 80 except that the reading unit 45 is driven in a state in which no subject is placed and no X-rays are emitted. The first offset image acquisition unit 93 performs a first offset image acquisition process of reading the pixel signal S from the pixel region 40, which has not been irradiated with X-rays, to acquire the first offset image OP1.

The second offset image acquisition unit 94 drives the reading unit 45 using the same reading method (that is, the binning reading method) as the immediately preceding offset image acquisition unit 95 except that the reading unit 45 is driven in a state in which no subject is placed. The second offset image acquisition unit 94 performs a second offset image acquisition process of reading the added pixel signal AS from the pixel region 40, which has not been irradiated with X-rays, to acquire the second offset image OP2.

The second offset image acquisition unit 94 operates immediately before the first offset image acquisition process of the first offset image acquisition unit 93 in a state in which no X-rays are emitted. The second offset image acquisition unit 94 repeatedly performs the second offset image acquisition process a plurality of times to acquire a plurality of second offset images OP2, similarly to the immediately preceding offset image acquisition unit 95.

The first offset image acquisition unit 93 and the second offset image acquisition unit 94 perform the same process (see FIG. 10) as the X-ray image generation unit 80 and the immediately preceding offset image acquisition unit 95 except that they operate in a state in which no subject is placed and no X-rays are emitted. The first offset image acquisition unit 93 and the second offset image acquisition unit 94 store the acquired first offset image OP1 and second offset image OP2 in the correction image storage unit 87.

In addition, in this embodiment, the first offset image acquisition unit 93 and the second offset image acquisition unit 94 drive the reading unit 45 in a state in which the gates (the gate electrodes of the TFTs 52) of all of the pixels 50 included in the pixel region 40 are turned off to acquire the first offset image OP1 and the second offset image OP2, respectively. The first offset image acquisition unit 93 and the second offset image acquisition unit 94 drive the reading unit 45 using the same reading method as the X-ray image generation unit 80 and the immediately preceding offset image acquisition unit 95 except that the gate driver 41 does not apply the gate pulses to the scanning lines 53.

Figure 17:
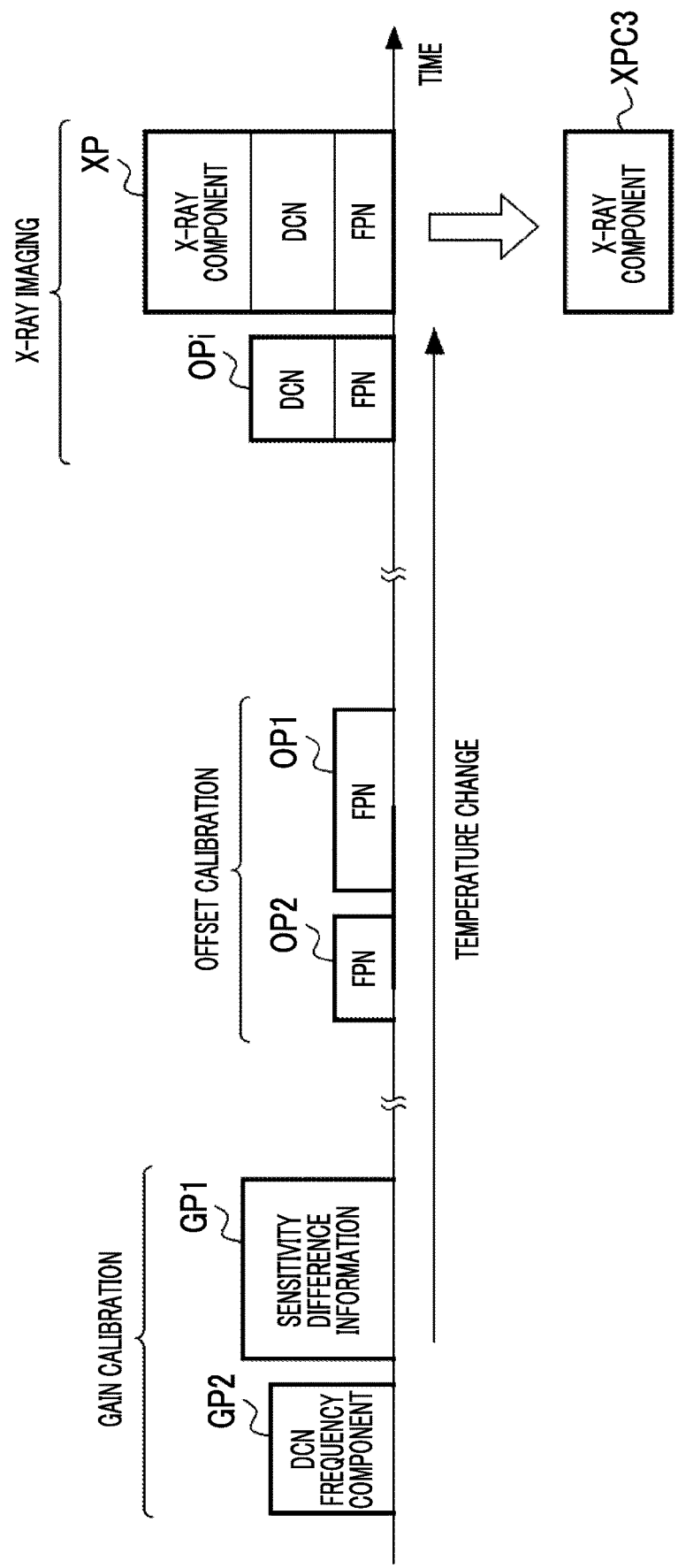
FIG. 17 is a schematic diagram illustrating noise components included in an X-ray image, an immediately preceding offset image, a first offset image, a second offset image, a first gain image, and a second gain image.

Since the first offset image OP1 and the second offset image OP2 are acquired in a state in which the gates of all of the pixels 50 are turned off, they do not include the DCN and mainly include the FPN (see FIG. 17).

The X-ray image XP includes the DCN and the FPN in addition to the X-ray component (that is, subject information) caused by the X-rays transmitted through the subject. Since the immediately preceding offset image OPi is acquired in a state in which no X-rays are emitted, it includes only the DCN and the FPN.

Since the first gain image GP1 is acquired in a state in which no subject is placed, it includes the sensitivity difference information indicating the difference in the sensitivity of each pixel 50 to the X-rays. As described above, the second gain image GP2 includes the high frequency noise caused by the dark current due to the residual image. This high frequency noise corresponds to a component that is caused by the dark current in the sensitivity difference information.

In addition, the high frequency noise generated by the flow of the dark current from the pixel region 40 to the reading unit 45 is also included in the first gain image GP1, the immediately preceding offset image OPi, and the X-ray image XP.

Figure 12:
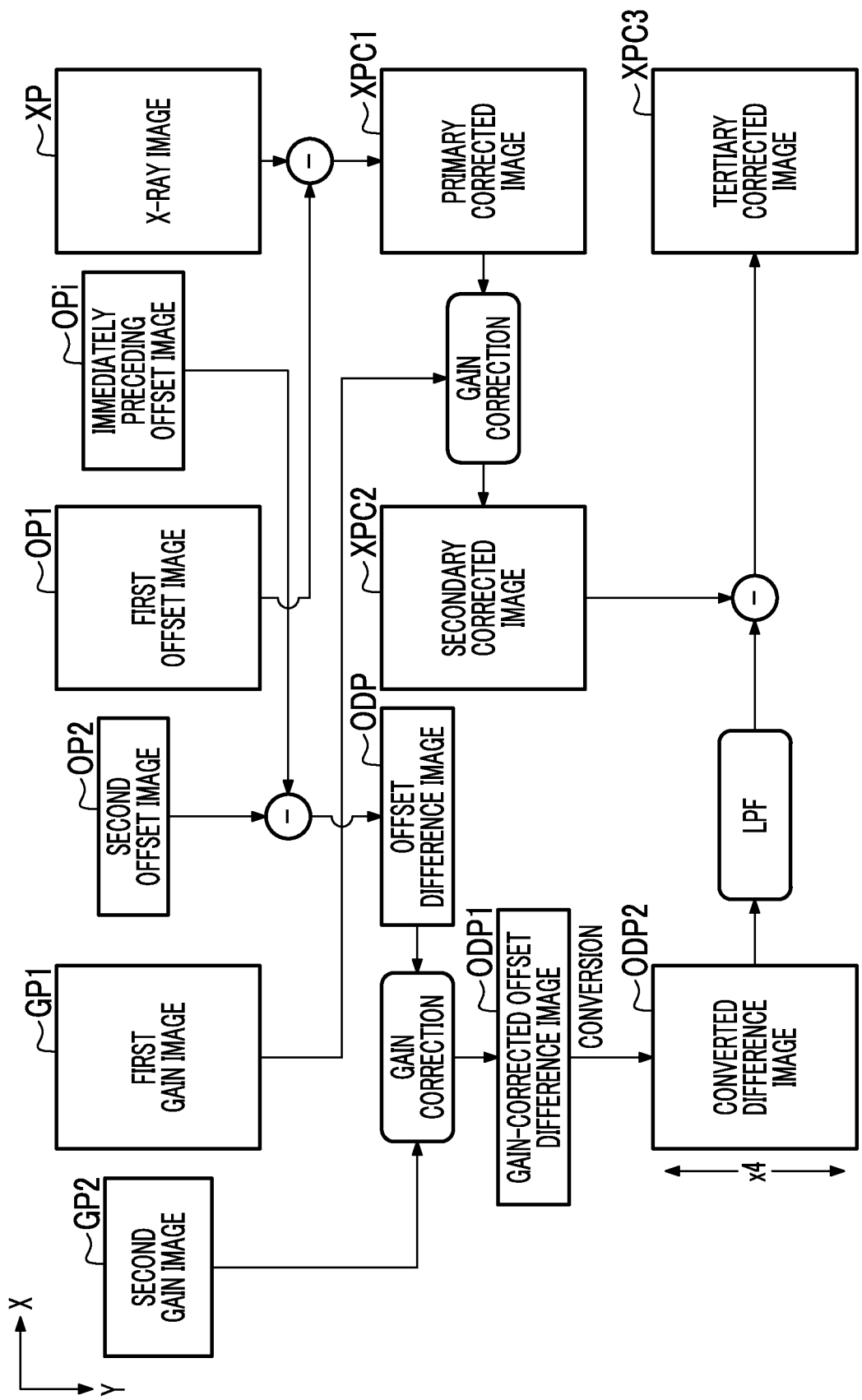
FIG. 12 is a schematic diagram illustrating the outline of a correction process.

FIG. 12 illustrates the outline of the correction process of the correction processing unit 100. The correction processing unit 100 performs a correction process of correcting the X-ray image XP on the basis of the first offset image OP1, the second offset image OP2, the immediately preceding offset image OPi, the first gain image GP1, and the second gain image GP2.

Figure 13:
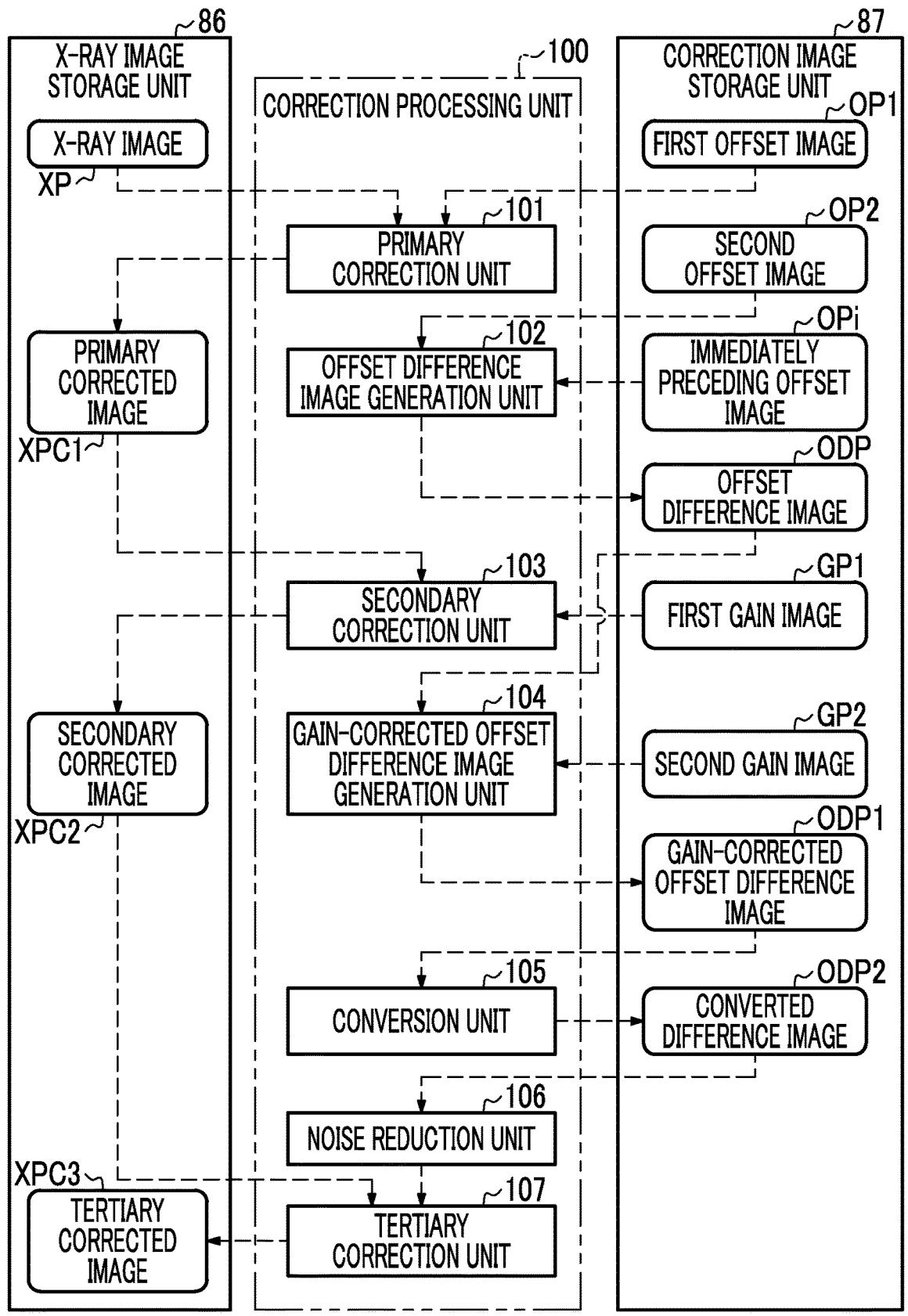
FIG. 13 is a block diagram illustrating a functional configuration of a correction processing unit.

As illustrated in FIG. 13, the correction processing unit 100 includes a primary correction unit 101, an offset difference image generation unit 102, a secondary correction unit 103, a gain-corrected offset difference image generation unit 104, a conversion unit 105, a noise reduction unit 106, and a tertiary correction unit 107.

The primary correction unit 101 acquires the X-ray image XP from the X-ray image storage unit 86 and also acquires the first offset image OP1 from the correction image storage unit 87. The primary correction unit 101 performs a primary correction process of subtracting the first offset image OP1 from the X-ray image XP to generate a primary corrected image XPC1. The primary correction unit 101 stores the generated primary corrected image XPC1 in the X-ray image storage unit 86.

The offset difference image generation unit 102 acquires the second offset image OP2 and the immediately preceding offset image OPi from the correction image storage unit 87. The immediately preceding offset image OPi acquired most immediately before the start of irradiation with X-rays is affected by the irradiation with X-rays (see FIG. 7). Therefore, the offset difference image generation unit 102 selects the immediately preceding offset image OPi other than most immediately before the start of the irradiation with X-rays.

The offset difference image generation unit 102 performs an offset difference image generation process of subtracting the second offset image OP2 from the immediately preceding offset image OPi to generate an offset difference image ODP. The offset difference image generation unit 102 stores the generated offset difference image ODP in the correction image storage unit 87. In addition, the offset difference image generation unit 102 may perform the offset difference image generation process using an average image obtained by averaging a plurality of immediately preceding offset images OPi.

The secondary correction unit 103 acquires the primary corrected image XPC1 from the X-ray image storage unit 86 and also acquires the first gain image GP1 from the correction image storage unit 87. The secondary correction unit 103 performs a secondary correction process of performing gain correction on the primary corrected image XPC1 on the basis of the first gain image GP1 to generate a secondary corrected image XPC2. Specifically, the secondary correction unit 103 calculates a correction coefficient for each pixel on the basis of the first gain image GP1 and performs the gain correction on each pixel value of the primary corrected image XPC1 on the basis of the calculated correction coefficient to generate the secondary corrected image XPC2. The secondary correction unit 103 stores the generated secondary corrected image XPC2 in the X-ray image storage unit 86.

The gain-corrected offset difference image generation unit 104 acquires the offset difference image ODP and the second gain image GP2 from the correction image storage unit 87. The gain-corrected offset difference image generation unit 104 performs a gain-corrected offset difference image generation process of performing gain correction on the offset difference image ODP on the basis of the second gain image GP2 to generate a gain-corrected offset difference image ODP1.

Specifically, the gain-corrected offset difference image generation unit 104 calculates a correction coefficient for each pixel on the basis of the second gain image GP2 and performs gain correction on each pixel value of the offset difference image ODP on the basis of the calculated correction coefficient to generate the gain-corrected offset difference image ODP1. The gain-corrected offset difference image generation unit 104 stores the generated gain-corrected offset difference image ODP1 in the correction image storage unit 87. In addition, the gain-corrected offset difference image generation unit 104 may perform the gain-corrected offset difference image generation process using an average image obtained by averaging a plurality of second gain images GP2.

The conversion unit 105 acquires the gain-corrected offset difference image ODP1 from the correction image storage unit 87 and performs at least one of an accumulation time multiplication process or an enlargement and reduction process for adjusting an image size to the X-ray image XP on the acquired gain-corrected offset difference image ODP1. In this embodiment, both the multiplication process and the enlargement and reduction process are performed on the gain-corrected offset difference image ODP1.

The conversion unit 105 performs a multiplication process of multiplying each pixel value of the gain-corrected offset difference image ODP1 by the ratio (AT1/AT2) of the accumulation period AT1 in the X-ray imaging to the accumulation period AT2 in the acquisition of the immediately preceding offset image OPi as a coefficient. In addition, the conversion unit 105 performs an enlargement process of enlarging the gain-corrected offset difference image ODP1 in the direction (the Y direction in this embodiment) in which the image has been reduced by the binning reading to adjust the image size of the gain-corrected offset difference image ODP1 to the image size of the X-ray image XP (see FIG. 12). This enlargement process is performed, for example, by a complement process.

In addition, the conversion unit 105 multiplies a conversion coefficient corresponding to the difference between the reading method (sequential reading method) in the X-ray imaging and the reading method (binning reading method) in the acquisition of the immediately preceding offset image OPi. In the sequential reading method, the charge corresponding to one pixel is converted into a pixel signal by the signal processing circuit 42. In contrast, in the binning reading method, the charge output from a plurality of pixels is added and converted into a pixel signal by the signal processing circuit 42. The conversion characteristics of the signal processing circuit 42 converting the charge into the pixel signal are not necessarily linear. For example, the added pixel signal based on the charge corresponding to four pixels is likely to deviate from a value that is four times as large as the pixel signal based on the charge corresponding to one pixel. Therefore, the conversion unit 105 multiplies each pixel value of the gain-corrected offset difference image ODP1 by a conversion coefficient for correcting the nonlinearity of the conversion characteristics of the signal processing circuit 42. The conversion unit 105 stores a converted difference image ODP2 obtained by converting the gain-corrected offset difference image ODP1 in the correction image storage unit 87.

The noise reduction unit 106 performs a noise reduction process of acquiring the converted difference image ODP2 from the correction image storage unit 87 and performing a low-pass filtering process on the acquired converted difference image ODP2 to reduce high frequency noise. The high frequency noise reduced by the noise reduction unit 106 includes, for example, high frequency noise generated by a conversion error of the A/D converter 67 and high frequency noise caused by the flow of the dark current from the pixel region 40 to the reading unit 45.

The tertiary correction unit 107 acquires the secondary corrected image XPC2 from the X-ray image storage unit 86. The tertiary correction unit 107 performs a tertiary correction process of subtracting the converted difference image ODP2 subjected to the low-pass filtering process by the noise reduction unit 106 from the secondary corrected image XPC2 to generate a tertiary corrected image XPC3. The tertiary correction unit 107 stores the generated tertiary corrected image XPC3 in the X-ray image storage unit 86. The tertiary corrected image XPC3 is the final corrected X-ray image obtained by the correction processing unit 100. For example, the tertiary corrected image XPC3 is displayed on the display 14B (see FIG. 1).

Figure 14:
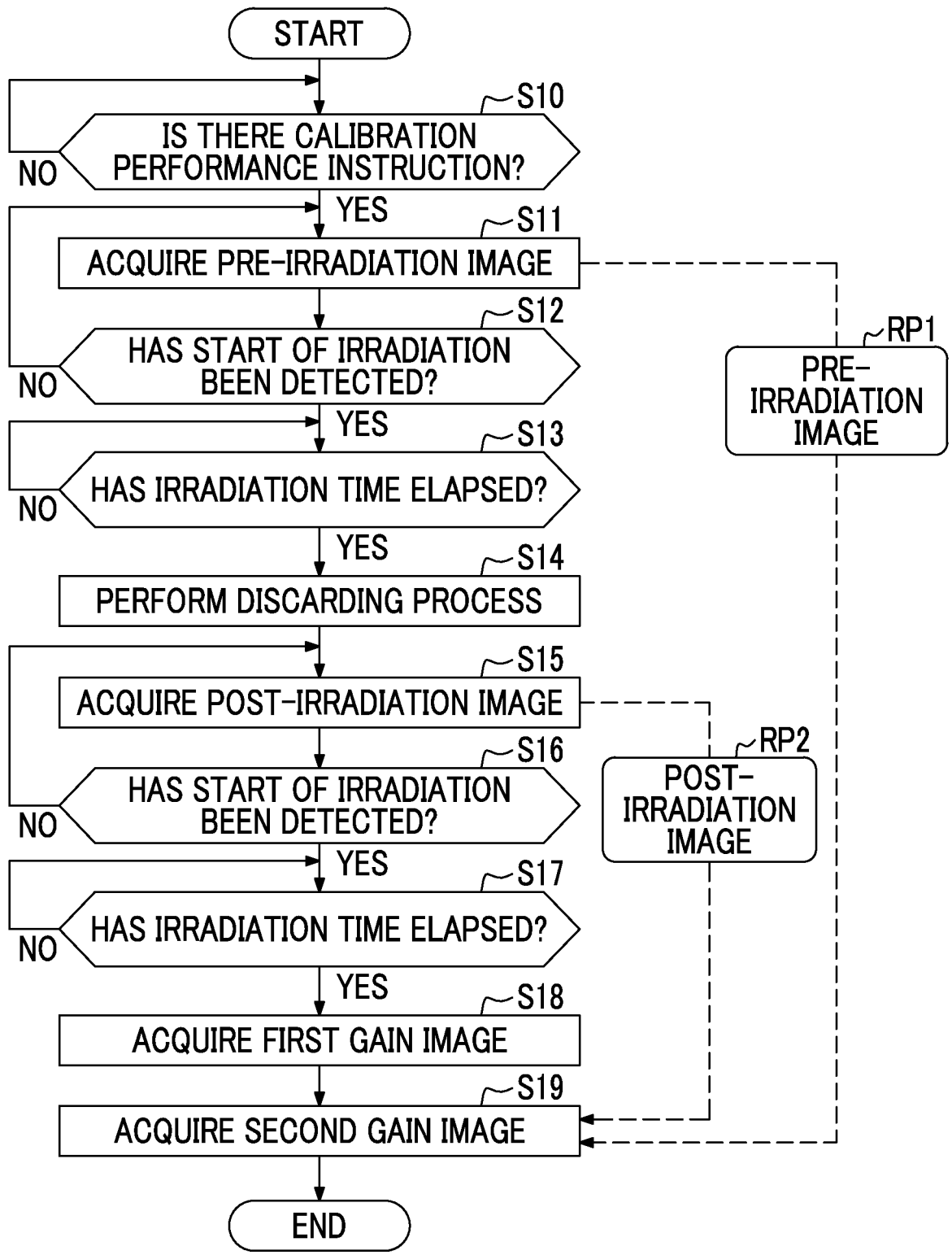
FIG. 14 is a flowchart illustrating a processing procedure during gain calibration.
Figure 15:
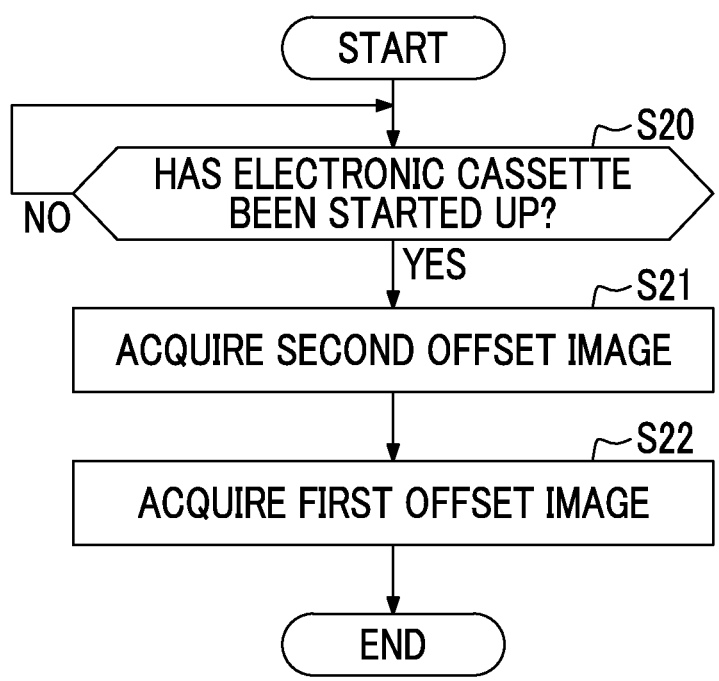
FIG. 15 is a flowchart illustrating a processing procedure during offset calibration.
Figure 16:
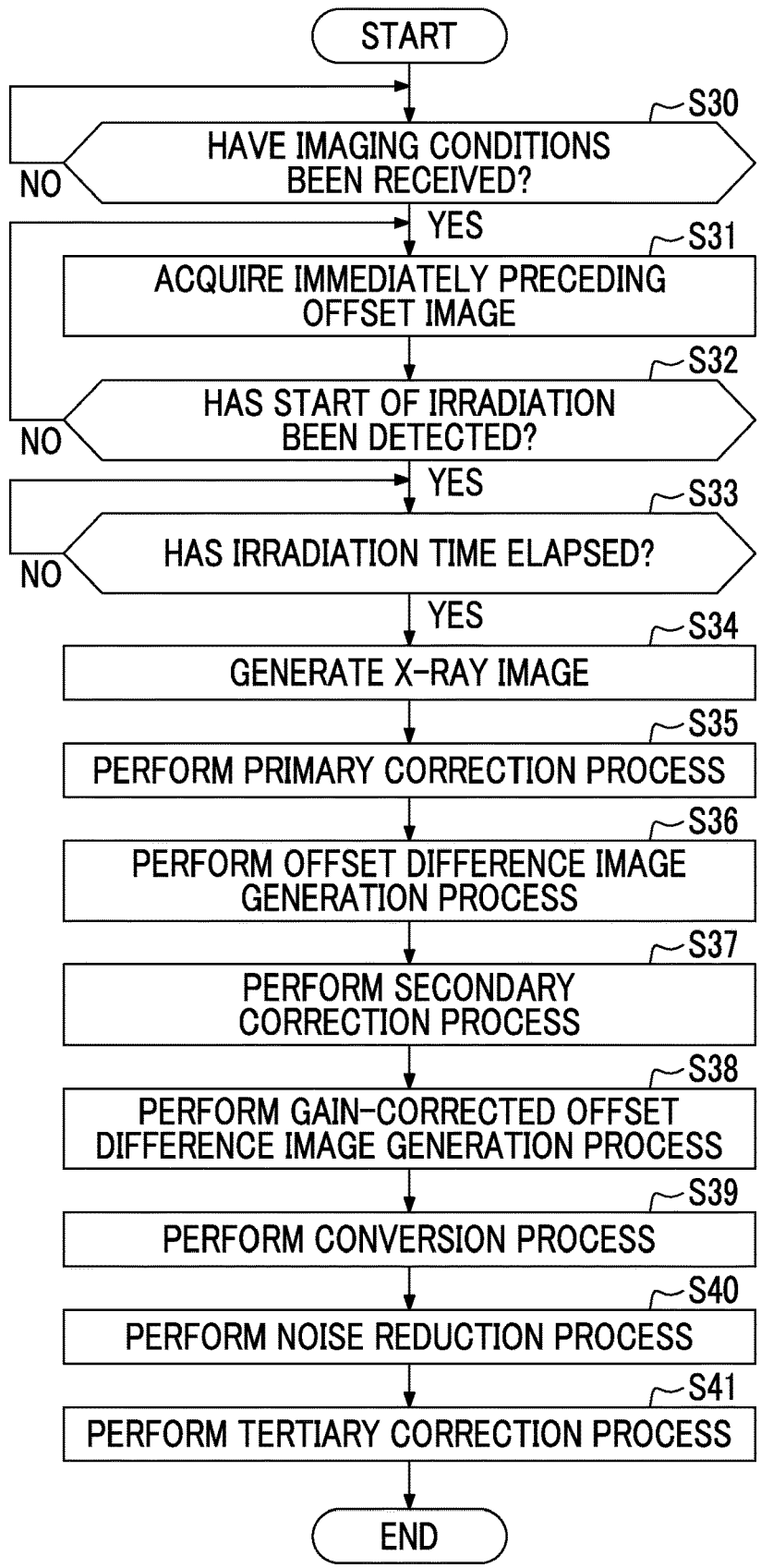
FIG. 16 is a flowchart illustrating a processing procedure during X-ray imaging.

Next, the operation of the X-ray imaging system 2 having the above-mentioned configuration will be described with reference to flowcharts illustrated in FIGS. 14, 15, and 16. FIG. 14 is a flowchart illustrating a processing procedure during the gain calibration. FIG. 15 is a flowchart illustrating a processing procedure during the offset calibration. FIG. 16 is a flowchart illustrating a processing procedure during the X-ray imaging.

In addition, the operator adjusts the position of the X-ray source 10 and the size of the irradiation field according to the position of the electronic cassette 13 and the size of an imaging part of the subject in a case in which the gain calibration is started. Then, the operator operates the input device 14A of the console 14 to instruct the performance of the gain calibration.

As illustrated in FIG. 14, the control unit 43 of the electronic cassette 13 waits for a gain calibration performance instruction signal transmitted from the console 14 (Step S10). In a case in which the control unit 43 receives the performance instruction signal from the console 14 through the communication I/F 44 (Step S10: YES), the pre-irradiation image acquisition unit 92A drives the reading unit 45 using the binning reading method to acquire the pre-irradiation image RP1 (Step S11).

The irradiation start detection unit 82 operates during the binning reading operation of acquiring the pre-irradiation image RP1 to detect the start of irradiation with X-rays on the basis of the added pixel signal AS obtained during the binning reading (Step S12). In a case in which the irradiation start detection unit 82 does not detect the start of irradiation with X-rays (Step S12: NO), the process of acquiring the pre-irradiation image RP1 in Step S11 is repeated. The acquired pre-irradiation image RP1 is stored in the correction image storage unit 87.

The operator presses the irradiation switch 12 halfway to instruct preparation for irradiation with X-rays for gain calibration. In a case in which the irradiation switch 12 is pressed halfway, a warm-up instruction signal is issued to the high voltage generator 21, and the warm-up of the X-ray source 10 is started. Then, in a case in which the operator fully presses the irradiation switch 12, a large dose of X-rays that saturates the charge accumulated in each pixel 50 is emitted from the X-ray source 10 to the electronic cassette 13.

In a case in which the irradiation start detection unit 82 detects the start of irradiation with X-rays (Step S12: YES), the pre-irradiation image acquisition unit 92A stops the binning reading, and the discarding unit 92B starts measuring the irradiation time using the timer 73. Then, the pixel region 40 is changed to a charge accumulation state. The charge accumulated in each pixel 50 is saturated by irradiation with a large dose of X-rays. The discarding unit 92B determines whether or not a predetermined irradiation time has elapsed (Step S13).

In a case in which it is determined that the irradiation time has elapsed (Step S13: YES), the discarding unit 92B performs a discarding process of driving the reading unit 45 using, for example, the sequential reading method to read the pixel signal S from each pixel 50 and discarding the pixel signal S (Step S14). The charge accumulated in each pixel 50 is discarded by this process. Then, a residual charge (residual image) in the TFT 52 or the like of each pixel 50 flows as the dark current to the integrator 60 or the like through each signal line 54. As a result, high frequency noise is generated.

After the discarding unit 92B performs the charge discarding process, the post-irradiation image acquisition unit 92C drives the reading unit 45 using the binning reading method to acquire the post-irradiation image RP2 (Step S15). The post-irradiation image RP2 includes high frequency noise caused by the dark current due to the residual image.

The irradiation start detection unit 82 operates during the binning reading operation of acquiring the post-irradiation image RP2 to detect the start of irradiation with X-rays on the basis of the added pixel signal AS obtained during the binning reading (Step S16). In a case in which the irradiation start detection unit 82 does not detect the start of irradiation with X-rays (Step S16: NO), the process of acquiring the post-irradiation image RP2 in Step S15 is repeated. The acquired post-irradiation image RP2 is stored in the correction image storage unit 87.

Then, the same dose of X-rays as that in the X-ray imaging is emitted from the X-ray source 10 to the electronic cassette 13. In a case in which the irradiation start detection unit 82 detects the start of irradiation with X-rays (Step S16: YES), the post-irradiation image acquisition unit 92C stops the binning reading, and the first gain image acquisition unit 91 starts measuring the irradiation time using the timer 73. Then, the pixel region 40 is changed to the charge accumulation state. Each pixel 50 accumulates charge corresponding to the amount of X-rays emitted. The first gain image acquisition unit 91 determines whether or not a predetermined irradiation time has elapsed (Step S17).

In a case in which it is determined that the irradiation time has elapsed (Step S17: YES), the first gain image acquisition unit 91 drives the reading unit 45 using the sequential reading method to acquire and generate the first gain image GP1 (Step S18). The acquired first gain image GP1 is stored in the correction image storage unit 87.

Then, the second gain image acquisition unit 92 acquires the pre-irradiation image RP1 and the post-irradiation image RP2 from the correction image storage unit 87 and subtracts the pre-irradiation image RP1 from the post-irradiation image RP2 to acquire the second gain image GP2 (Step S19). The second gain image GP2 mainly includes the high frequency noise caused by the dark current due to the residual image. The second gain image acquisition unit 92 stores the acquired second gain image GP2 in the correction image storage unit 87. In this way, the gain calibration process ends.

Then, offset calibration is performed, for example, in a case in which the electronic cassette 13 is started up. As illustrated in FIG. 15, the control unit 43 of the electronic cassette 13 determines whether or not the electronic cassette 13 has been started up by the pressure of the power switch 33 (see FIG. 3) of the electronic cassette 13 by the operator (Step S20).

In a case in which the control unit 43 determines that the electronic cassette 13 has been started up (Step S20: YES), the second offset image acquisition unit 94 drives the reading unit 45 using the binning reading method to acquire the second offset image OP2 (Step S21). The acquired second offset image OP2 is stored in the correction image storage unit 87.

Then, the first offset image acquisition unit 93 drives the reading unit 45 using the sequential reading method to acquire the first offset image OP1 (Step S22). The acquired first offset image OP1 is stored in the correction image storage unit 87. In this way, the offset calibration process ends.

After the offset calibration ends, in the X-ray imaging, the operator sets the subject at the imaging position of the upright imaging stand 15 or the decubitus imaging stand 16 and adjusts the position of the electronic cassette 13. In addition, the operator adjusts the position of the X-ray source 10 and the size of the irradiation field according to the position of the electronic cassette 13 and the size of an imaging part of the subject. Then, the operator sets imaging conditions in the radiation source control device 11 and the console 14. The imaging conditions set in the console 14 are transmitted to the electronic cassette 13.

As illustrated in FIG. 16, the control unit 43 of the electronic cassette 13 waits for the imaging conditions transmitted from the console 14 (Step S30). In a case in which the control unit 43 receives the imaging conditions from the console 14 through the communication I/F 44 (Step S30: YES), the immediately preceding offset image acquisition unit 95 drives the reading unit 45 using the binning reading method to acquire the immediately preceding offset image OPi (Step S31).

The irradiation start detection unit 82 operates during the binning reading operation to detect the start of irradiation with X-rays on the basis of the added pixel signal AS obtained during the binning reading (Step S32). In a case in which the irradiation start detection unit 82 does not detect the start of irradiation with X-rays (Step S32: NO), the process of acquiring the immediately preceding offset image OPi in Step S31 is repeated.

In the X-ray imaging, the operator presses the irradiation switch 12 halfway to instruct preparation for imaging. In a case in which the irradiation switch 12 is pressed halfway, a warm-up instruction signal is issued to the high voltage generator 21, and the warm-up of the X-ray source 10 is started. Then, in a case in which the operator fully presses the irradiation switch 12, X-rays are emitted from the X-ray source 10 to the subject.

In a case in which the irradiation start detection unit 82 detects the start of irradiation with X-rays (Step S32: YES), the X-ray image generation unit 80 stops the binning reading and starts measuring the irradiation time using the timer 73. Then, the pixel region 40 is changed to the charge accumulation state and accumulates charge corresponding to the amount of X-rays emitted through the subject. The X-ray image generation unit 80 determines whether or not the irradiation time included in the imaging conditions has elapsed (Step S33).

In a case in which the X-ray image generation unit 80 determines that the irradiation time has elapsed (Step S33: YES), it drives the reading unit 45 using the sequential reading method to generate the X-ray image XP (Step S34).

Then, the primary correction unit 101 subtracts the first offset image OP1 from the X-ray image XP to generate the primary corrected image XPC1 (Step S35). Then, the offset difference image generation unit 102 subtracts the second offset image OP2 from the immediately preceding offset image OPi to generate the offset difference image ODP (Step S36).

Then, the secondary correction unit 103 performs gain correction on the primary corrected image XPC1 on the basis of the first gain image GP1 to generate the secondary corrected image XPC2 (Step S37). Then, the gain-corrected offset difference image generation unit 104 performs gain correction on the offset difference image ODP on the basis of the second gain image GP2 to generate the gain-corrected offset difference image ODP1 (Step S38).

Then, the conversion unit 105 performs the accumulation time multiplication process and the enlargement and reduction process for adjusting the image size to the X-ray image XP on the gain-corrected offset difference image ODP1 to generate the converted difference image ODP2 (Step S39). Then, the noise reduction unit 106 performs a noise reduction process of performing a low-pass filtering process on the converted difference image ODP2 to reduce high frequency noise (Step S40). In the low-pass filtering process, for example, high frequency random noise that remains after the gain correction is removed.

Then, the tertiary correction unit 107 subtracts the converted difference image ODP2 subjected to the low-pass filtering process from the secondary corrected image XPC2 to generate the tertiary corrected image XPC3 (Step S41). In this way, the X-ray imaging operation ends.

FIG. 17 is a schematic diagram illustrating noise components included in the X-ray image XP, the immediately preceding offset image OPi, the first offset image OP1, the second offset image OP2, the first gain image GP1, and the second gain image GP2.

Since the immediately preceding offset image OPi is acquired in a state in which no X-rays are emitted, it mainly includes the DCN and the FPN. The X-ray image XP includes the DCN and the FPN in addition to an X-ray component including subject information. Since the first offset image OP1 and the second offset image OP2 are acquired in a state in which no X-rays are emitted and the gates of all of the pixels 50 are turned off, they include only the FPN.

The first gain image GP1 includes the sensitivity difference information indicating the difference in the sensitivity of each pixel 50 to X-rays. The second gain image GP2 mainly includes high frequency noise caused by the dark current due to the residual image.

In addition, in the first gain image GP1, the immediately preceding offset image OPi, and the X-ray image XP, high frequency noise generated by the flow of the dark current from the pixel region 40 to the reading unit 45 is included in the DCN.

The gain calibration is performed, for example, only during the maintenance of the X-ray imaging system 2. In a case in which the temperature is different between the gain calibration and the X-ray imaging, the DCN changes. In particular, since the electronic cassette 13 is portable and small in size, it has a small heat capacity. Therefore, the electronic cassette 13 is likely to be affected by an environmental temperature change. Further, since the electronic cassette 13 periodically detects the start of irradiation, it consumes a large amount of power and generates heat. Therefore, a temperature change is likely to occur. As such, in the electronic cassette 13, the amount of variation in DCN is large. Therefore, it is difficult to correct the DCN included in the X-ray image XP with high accuracy, using only the offset image acquired during the calibration.

In the electronic cassette 13 according to this embodiment, the X-ray image XP is corrected on the basis of the immediately preceding offset image OPi acquired in a state in which no X-rays are emitted immediately before the X-ray imaging. Therefore, it is possible to correct the DCN included in the X-ray image XP with high accuracy.

Further, in the electronic cassette 13 according to this embodiment, the first offset image OP1 and the second offset image OP2 including the FPN are acquired by the offset calibration. The first offset image OP1 and the second offset image OP2 are subtracted from the X-ray image XP and the immediately preceding offset image OPi to generate the primary corrected image XPC1 and the offset difference image ODP without including the FPN, respectively.

In this embodiment, gain correction is performed on the primary corrected image XPC1 and the offset difference image ODP on the basis of the first gain image GP1 and the second gain image GP2 acquired during the gain calibration, respectively.

The second gain image GP2 is generated by subtracting the pre-irradiation image RP1 acquired before a large dose X-rays is emitted from the post-irradiation image RP2 acquired after a large dose X-rays is emitted and the charge in each pixel 50 is discarded. Therefore, the second gain image GP2 mainly includes high frequency noise caused by the dark current due to the residual image. As a result, the use of the second gain image GP2 makes it possible to perform gain correction on the immediately preceding offset image OPi with high accuracy.

Further, in this embodiment, the low-pass filtering process is performed on the gain-corrected offset difference image ODP1 (in this embodiment, the converted difference image ODP2 further subjected to the conversion process). The low-pass filtering process is a noise reduction process for removing high frequency noise. Therefore, in a case in which the low-pass filtering process is performed before the gain correction, the high frequency noise included in the DCN is removed. The high frequency noise included in this DCN is also included in the first gain image GP1 and the second gain image GP2. Therefore, in a case in which the gain correction is performed on the offset difference image ODP subjected to the low-pass filtering process, the high frequency noise is excessively corrected. As a result, the high frequency noise remains as a correction error.

In this embodiment, after the gain correction is performed on the offset difference image ODP to remove the high frequency noise included in the DCN, the low-pass filtering process is performed. Therefore, it is possible to reduce the correction error of the high frequency noise. In the low-pass filtering process, for example, high frequency random noise that remains after the gain correction is removed. As a result, the tertiary corrected image XPC3 in which high frequency noise has been reduced with high accuracy is obtained.

In the above-described embodiment, the conversion unit 105 performs the conversion process on the gain-corrected offset difference image ODP1 before the noise reduction unit 106 performs the low-pass filtering process. Instead of this configuration, the conversion unit 105 may perform the conversion process on the gain-corrected offset difference image ODP1 subjected to the low-pass filtering process by the noise reduction unit 106.

Further, in the above-described embodiment, during the offset calibration, the first offset image OP1 and the second offset image OP2 are acquired by driving the reading unit 45 in a state in which the gates of all of the pixels 50 are turned off. Instead of this configuration, the first offset image OP1 and the second offset image OP2 may be acquired by driving the reading unit 45 using the same reading method as that used for the X-ray image XP and the immediately preceding offset image OPi in a state in which the gates of the pixels 50 as the reading targets are turned on. In this case, the first offset image OP1 and the second offset image OP2 include the DCN and the FPN. Further, in this case, the primary corrected image XPC1 and the offset difference image ODP include the amount of variation in DCN from the offset calibration.

Figure 18:
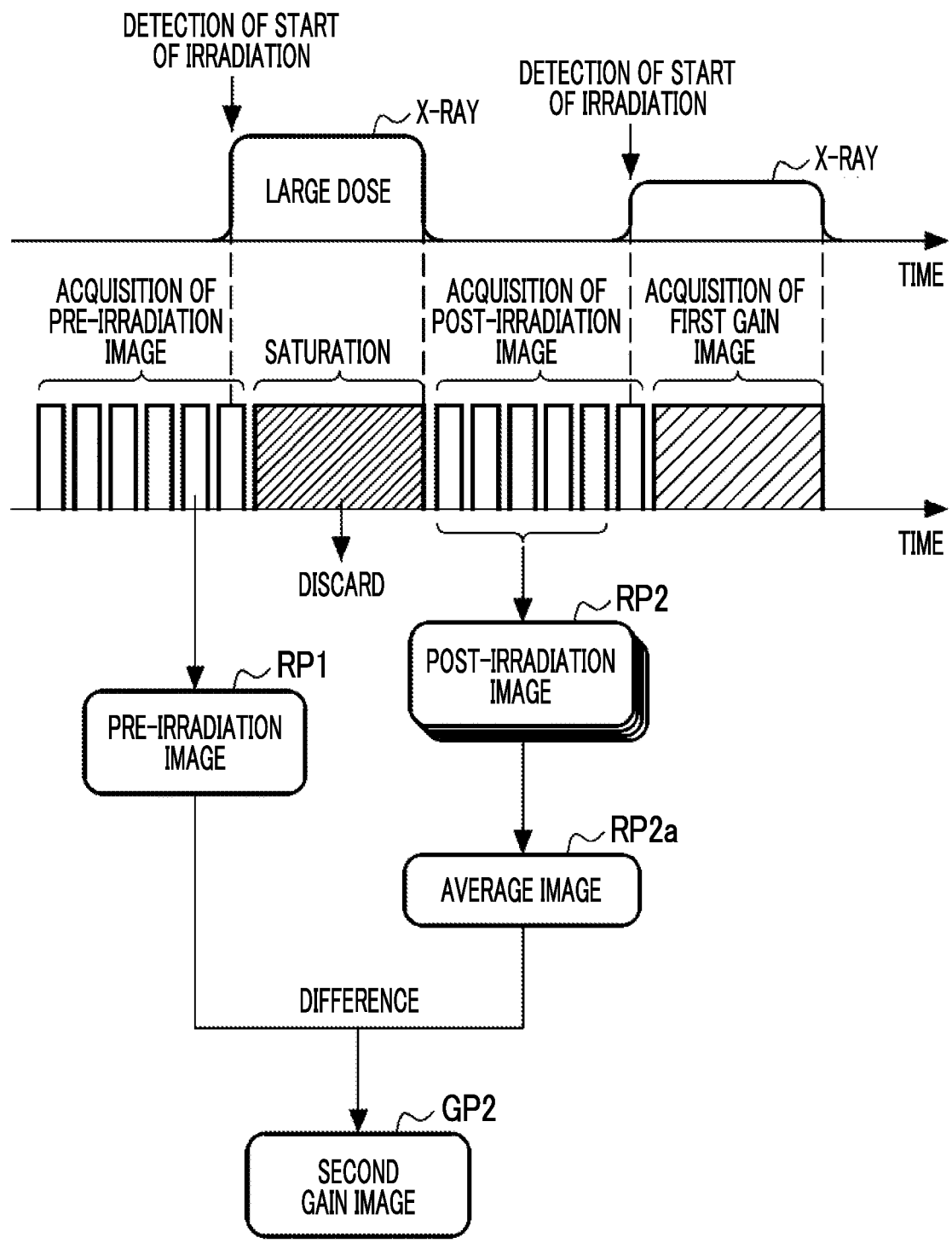
FIG. 18 is a schematic diagram illustrating a first modification example related to a second gain image acquisition process.

In addition, in the above-described embodiment, the second gain image acquisition unit 92 subtracts one pre-irradiation image RP1 from one post-irradiation image RP2 to acquire the second gain image GP2. Instead of this configuration, as illustrated in FIG. 18, the second gain image acquisition unit 92 may subtract the pre-irradiation image RP1 from an average image RP2a obtained by averaging a plurality of post-irradiation images RP2 to acquire the second gain image GP2. After a large dose of X-rays is emitted, the residual image is gradually reduced. Therefore, since the plurality of post-irradiation images RP2 are averaged to average the residual images that are gradually reduced, the quality of the second gain image GP2 is improved.

Figure 19:
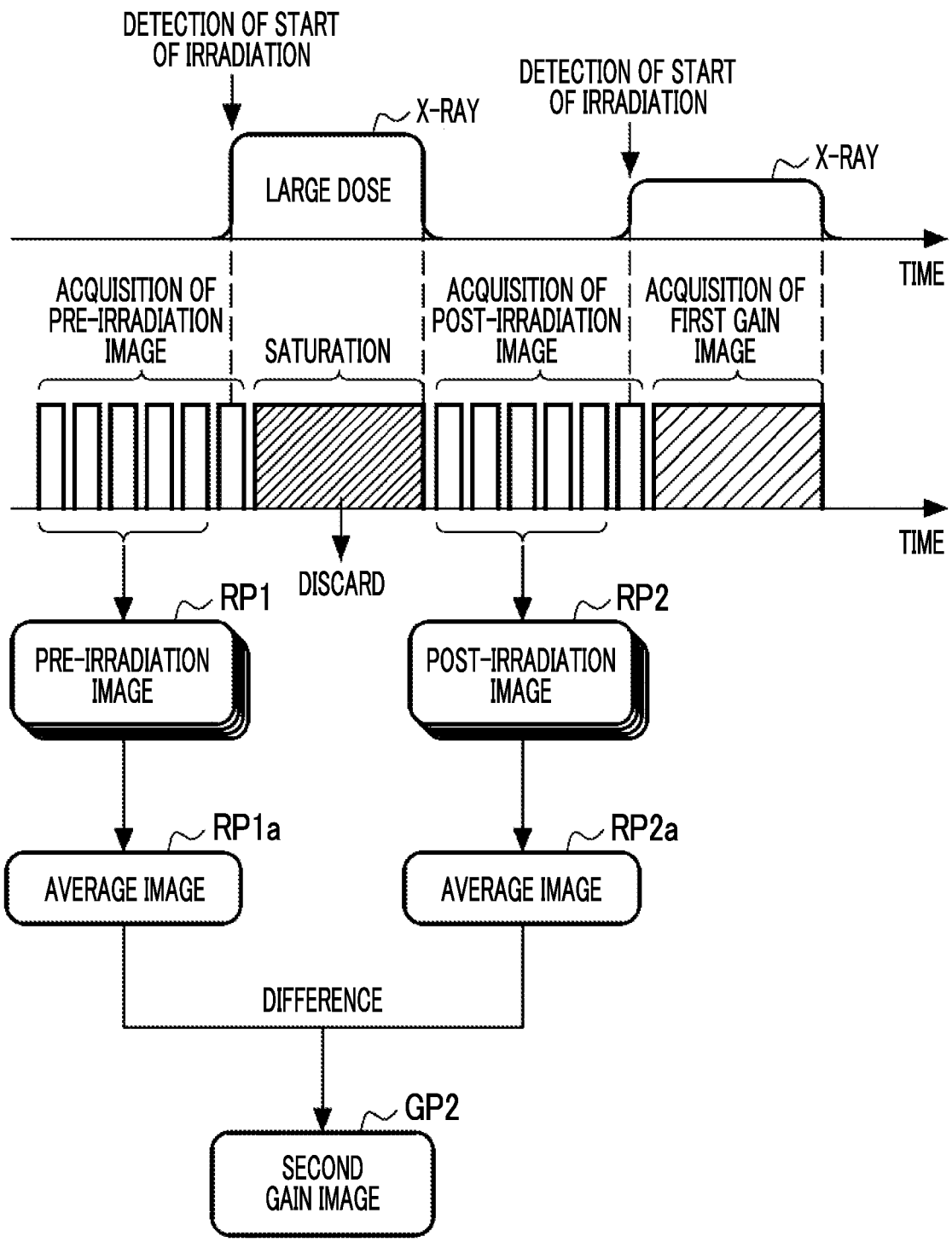
FIG. 19 is a schematic diagram illustrating a second modification example related to the second gain image acquisition process.

Further, as illustrated in FIG. 19, the second gain image acquisition unit 92 may subtract an average image RP1a obtained by averaging a plurality of pre-irradiation images RP1 from the average image RP2a obtained by averaging the plurality of post-irradiation images RP2 to acquire the second gain image GP2.

Furthermore, in the above-described embodiment, the offset correction and the gain correction are performed as the correction process. However, for example, defective pixel correction may be further performed.

Further, the technology of the present disclosure is not limited to X-rays and can be applied to a system that captures the image of the subject using other kinds of radiation such as γ-rays.

In the above-described embodiment, for example, the following various processors can be used as a hardware structure of processing units performing various processes, such as the X-ray image generation unit 80, the irradiation start detection unit 82, the correction image acquisition processing unit 90, and the correction processing unit 100.

The various processors include, for example, a CPU, a programmable logic device (PLD), a dedicated electric circuit. As is well known, the CPU is a general-purpose processor that executes software (program) to function as various processing units. The PLD is a processor such as a field programmable gate array (FPGA) whose circuit configuration can be changed after manufacture. The dedicated electric circuit is a processor that has a dedicated circuit configuration designed to perform a specific process, such as an application specific integrated circuit (ASIC).

One processing unit may be configured by one of the various processors or a combination of two or more processors of the same type or different types (for example, a combination of a plurality of FPGAs and a combination of a CPU and an FPGA). Further, a plurality of processing units may be configured by one processor. A first example of the configuration in which a plurality of processing units are configured by one processor is an aspect in which one processor is configured by a combination of one or more CPUs and software and functions as a plurality of processing units. A second example of the configuration is an aspect in which a processor that implements the functions of the entire system including a plurality of processing units using one IC chip is used. A representative example of this aspect is a system-on-chip (SoC). As such, various processing units are configured by using one or more of the various processors as the hardware structure.

In addition, specifically, an electric circuit (circuitry) obtained by combining circuit elements, such as semiconductor elements, is used as the hardware structure of the various processors.

The technology of the present disclosure is not limited to the above-described embodiment and may adopt various configurations without departing from the spirit and scope of the present disclosure. Furthermore, the technology of the present disclosure extends to a computer-readable storage medium that non-temporarily stores the program, in addition to the program.

What is claimed is:

1. A radiographic image detection device that includes a pixel region, in which a plurality of pixels that accumulate charge corresponding to radiation emitted from a radiation source to detect the radiation are arranged, and performs radiography, which irradiates the pixel region with the radiation from the radiation source in a state in which a subject is placed between the radiation source and the pixel region and reads a pixel signal corresponding to the charge from the pixel region, to acquire a radiographic image of the subject, comprising:
   at least one processor,
   wherein the processor performs a correction image acquisition process of acquiring a correction image for correcting the radiographic image, and
   the correction image acquisition process includes:
   a first gain image acquisition process of reading the pixel signal from the pixel region irradiated with the radiation in a state in which the subject is not placed to acquire a first gain image;
   a pre-irradiation image acquisition process of reading the pixel signal from the pixel region in a state in which the subject is not placed and the radiation is not emitted to acquire a pre-irradiation image;
   a discarding process of discarding the charge accumulated in the pixels of the pixel region after a dose of the radiation that saturates the charge is emitted in a state in which the subject is not placed;
   a post-irradiation image acquisition process of reading the pixel signal from the pixel region to acquire a post-irradiation image after the discarding process is performed; and
   a second gain image acquisition process of subtracting the pre-irradiation image from the post-irradiation image to acquire a second gain image.

2. The radiographic image detection device according to claim 1,
   wherein, in the post-irradiation image acquisition process, after performing the discarding process, the processor repeatedly reads the pixel signal from the pixel region to acquire a plurality of the post-irradiation images, and
   in the second gain image acquisition process, the processor subtracts the pre-irradiation image from an average image obtained by averaging the plurality of post-irradiation images to acquire the second gain image.

3. The radiographic image detection device according to claim 1,
   wherein, in the pre-irradiation image acquisition process and the post-irradiation image acquisition process, the processor reads the pixel signal from the pixel region in an accumulation time shorter than that of the plurality of first gain images or using binning reading to acquire the pre-irradiation image and the post-irradiation image.

4. The radiographic image detection device according to claim 1,
   wherein the correction image acquisition process further includes:
   a first offset image acquisition process of reading the pixel signal from the pixel region using the same reading method as that used for the first gain image in a state in which the subject is not placed and the radiation is not emitted to acquire a first offset image for correction;
   a second offset image acquisition process of reading the pixel signal from the pixel region using the same reading method as that used for the second gain image in a state in which the subject is not placed and the radiation is not emitted to acquire a second offset image for correction; and
   an immediately preceding offset image acquisition process of reading the pixel signal from the pixel region using the same reading method as that used for the second gain image immediately before the radiography to acquire an immediately preceding offset image for correction, and
   the processor performs:
   a primary correction process of subtracting the first offset image from the radiographic image to generate a primary corrected radiographic image;
   an offset difference image generation process of subtracting the second offset image from the immediately preceding offset image to generate an offset difference image;
   a secondary correction process of performing gain correction on the primary corrected image on the basis of the first gain image to generate a secondary corrected image;
   a gain-corrected offset difference image generation process of performing gain correction on the offset difference image on the basis of the second gain image to generate a gain-corrected offset difference image;
   a noise reduction process of performing a low-pass filtering process on the gain-corrected offset difference image; and
   a tertiary correction process of subtracting the gain-corrected offset difference image subjected to the low-pass filtering process from the secondary corrected image to generate a tertiary corrected image.

5. The radiographic image detection device according to claim 4,
   wherein the processor performs the first offset image acquisition process and the second offset image acquisition process in a state in which gates of the pixels are turned off.

6. The radiographic image detection device according to claim 4,
   wherein the processor performs the noise reduction process on a converted image obtained by performing, on the gain-corrected offset difference image, a multiplication process based on a difference in accumulation time from the radiographic image or an enlargement and reduction process of adjusting an image size to the radiographic image and a process of multiplying a conversion coefficient based on a difference between the reading methods.

7. A method for operating a radiographic image detection device that includes a pixel region, in which a plurality of pixels that accumulate charge corresponding to radiation emitted from a radiation source to detect the radiation are arranged, and performs radiography, which irradiates the pixel region with the radiation from the radiation source in a state in which a subject is placed between the radiation source and the pixel region and reads a pixel signal corresponding to the charge from the pixel region, to acquire a radiographic image of the subject, the method comprising:
- a first gain image acquisition step of reading the pixel signal from the pixel region irradiated with the radiation in a state in which the subject is not placed to acquire a first gain image;
- a pre-irradiation image acquisition step of reading the pixel signal from the pixel region in a state in which the subject is not placed and the radiation is not emitted to acquire a pre-irradiation image;
- a discarding step of discarding the charge accumulated in the pixels of the pixel region after a dose of the radiation that saturates the charge is emitted in a state in which the subject is not placed;
- a post-irradiation image acquisition step of reading the pixel signal from the pixel region to acquire a post-irradiation image after the charge is discarded; and
- a second gain image acquisition step of subtracting the pre-irradiation image from the post-irradiation image to acquire a second gain image.

8. A non-transitory computer-readable storage medium storing an operation program for operating at least one processor included in a radiographic image detection device that includes a pixel region, in which a plurality of pixels that accumulate charge corresponding to radiation emitted from a radiation source to detect the radiation are arranged, and performs radiography, which irradiates the pixel region with the radiation from the radiation source in a state in which a subject is placed between the radiation source and the pixel region and reads a pixel signal corresponding to the charge from the pixel region, to acquire a radiographic image of the subject, the operation program causing the processor to perform:
- a first gain image acquisition process of reading the pixel signal from the pixel region irradiated with the radiation in a state in which the subject is not placed to acquire a first gain image;
- a pre-irradiation image acquisition process of reading the pixel signal from the pixel region in a state in which the subject is not placed and the radiation is not emitted to acquire a pre-irradiation image;
- a discarding process of discarding the charge accumulated in the pixels of the pixel region after a dose of the radiation that saturates the charge is emitted in a state in which the subject is not placed;
- a post-irradiation image acquisition process of reading the pixel signal from the pixel region to acquire a post-irradiation image after the discarding process is performed; and
- a second gain image acquisition process of subtracting the pre-irradiation image from the post-irradiation image to acquire a second gain image.

* * * * *